(12) United States Patent
Tsutsumi et al.

(10) Patent No.: US 7,670,624 B2
(45) Date of Patent: Mar. 2, 2010

(54) GASTROINTESTINAL-SPECIFIC MULTIPLE DRUG RELEASE SYSTEM

(75) Inventors: Keiko Tsutsumi, Norman, OK (US); James S. Chu, Norman, OK (US)

(73) Assignee: Astella Pharma Inc., Tokyo (JP)

( * ) Notice: Subject to any disclaimer, the term of this patent is extended or adjusted under 35 U.S.C. 154(b) by 1403 days.

(21) Appl. No.: 11/046,517

(22) Filed: Jan. 27, 2005

(65) Prior Publication Data

US 2005/0208133 A1 Sep. 22, 2005

Related U.S. Application Data

(60) Provisional application No. 60/540,682, filed on Jan. 29, 2004.

(51) Int. Cl.
*A61K 9/14* (2006.01)
*A61K 9/16* (2006.01)
*A61K 9/20* (2006.01)
*A61K 9/24* (2006.01)

(52) U.S. Cl. .................. 424/489; 424/464; 424/465; 424/471; 424/472; 424/490; 424/493; 424/497; 424/498

(58) Field of Classification Search ............... None
See application file for complete search history.

(56) References Cited

U.S. PATENT DOCUMENTS

| | | | |
|---|---|---|---|
| 3,431,338 A | | 3/1969 | Munzel et al. |
| 4,642,903 A | | 2/1987 | Davies |
| 4,808,416 A | | 2/1989 | Hata et al. |
| 4,863,744 A | | 9/1989 | Urquhart et al. |
| 4,968,508 A | | 11/1990 | Oren et al. |
| 5,501,861 A | | 3/1996 | Makino et al. |
| 5,525,634 A | | 6/1996 | Sintov et al. |
| 5,614,503 A | | 3/1997 | Chaudhary et al. |
| 5,654,004 A | | 8/1997 | Okayama et al. |
| 5,656,294 A | | 8/1997 | Friend et al. |
| 5,714,679 A | | 2/1998 | Nichols et al. |
| 5,736,388 A | | 4/1998 | Chada et al. |
| 5,834,186 A | | 11/1998 | George et al. |
| 5,840,322 A | | 11/1998 | Weiss et al. |
| 5,854,038 A | | 12/1998 | Sullenger et al. |
| 5,855,914 A | | 1/1999 | Koyama et al. |
| 5,866,619 A | | 2/1999 | Sintov et al. |
| 5,874,415 A | | 2/1999 | Kufe et al. |
| 5,958,453 A | | 9/1999 | Ohno et al. |
| 6,004,582 A | * | 12/1999 | Faour et al. ............... 424/473 |
| 6,096,722 A | | 8/2000 | Bennett et al. |
| 6,151,525 A | | 11/2000 | Soykan et al. |
| 6,180,621 B1 | | 1/2001 | Kawamoto et al. |
| 6,214,378 B1 | | 4/2001 | Tanida et al. |
| 6,248,357 B1 | | 6/2001 | Ohno et al. |
| 6,368,629 B1 | | 4/2002 | Watanabe et al. |
| 6,569,456 B2 | * | 5/2003 | Faour et al. ............... 424/473 |
| 6,586,004 B2 | | 7/2003 | Shimizu et al. |
| 6,794,367 B1 | | 9/2004 | Tanida et al. |
| 2005/0008702 A1 | * | 1/2005 | Faour et al. ............... 424/473 |
| 2005/0202082 A1 | | 9/2005 | Hibino et al. |

FOREIGN PATENT DOCUMENTS

| | | |
|---|---|---|
| EP | 0453001 A1 | 10/1991 |
| EP | 0460921 A2 | 12/1991 |
| EP | 0553777 A2 | 6/1993 |
| EP | 0745382 A1 | 12/1996 |
| EP | 0839526 A2 | 5/1998 |
| EP | 0960621 A2 | 1/1999 |
| EP | 0922464 A1 | 6/1999 |
| JP | 03-086837 | 4/1991 |
| JP | 04-66538 | 3/1992 |
| JP | 05-271054 | 10/1993 |
| JP | 05-310558 | 11/1993 |
| JP | 06-100601 | 4/1994 |
| JP | 06-218028 | 8/1994 |
| JP | 06-305962 | 11/1994 |
| JP | 07-017853 | 1/1995 |
| JP | 08-310969 | 11/1996 |
| JP | 09-048726 | 2/1997 |
| JP | 09-071523 | 3/1997 |
| JP | 11-012161 | 1/1999 |
| JP | 11-012162 | 1/1999 |
| JP | 11-035451 | 2/1999 |
| JP | 11-043429 | 2/1999 |
| JP | 2000-103731 | 4/2000 |
| JP | 2000-178183 | 6/2000 |
| WO | WO 91/16881 A1 | 11/1991 |
| WO | WO 95/20380 A1 | 3/1995 |
| WO | WO 00/06126 A1 | 2/2000 |

OTHER PUBLICATIONS

International Search Report; PCT/US05/02679; Mar. 15, 2006.
Deasy, P.B., et al, "Development of Coated Ketoprofen Pellets for Oral Colon-Specific Drug Delivery," Proceed. Int'l. Symp. Control. Rel. Bioact. Mater., 1997, vol. 24, pp. 279-280.
Tsushima, "New Molded Tablet and Corresponding Novel Method for Production," J. Jpn. Soc. Pharm. Mach. & Eng., vol. 10, No. 4, pp. 5-17, Abstract.

* cited by examiner

*Primary Examiner*—S. Tran
(74) *Attorney, Agent, or Firm*—Townsend and Townsend and Crew LLP

(57) ABSTRACT

The present invention provides compositions and methods for the multiple release of a drug in the gastrointestinal tract of a subject through the use of an oral multiple drug release system. The system provides site-specific release of the drug to both the small intestine and the colon in the form of multiple controlled doses for long-lasting efficacy, thereby reducing the drug dosing frequency.

42 Claims, 11 Drawing Sheets

*Manufacturing Flow*

*Manufacturing Flow*

GASTROINTESTINAL-SPECIFIC MULTIPLE DRUG RELEASE SYSTEM

CROSS-REFERENCES TO RELATED APPLICATIONS

The present application claims priority to U.S. Provisional Application No. 60/540,682, filed Jan. 29, 2004, which is herein incorporated by reference in its entirety for all purposes.

BACKGROUND OF THE INVENTION

In the past decade, rapid development has occurred in the field of drug delivery and release. In particular, a number of drug delivery and release systems have been developed that influence the control of drug release.

For the topical treatment of diseases and disorders such as ulcerative colitis, drug release in the colon of the gastrointestinal tract topically accumulates the drug in a high concentration without involving absorption in the small intestine, which leads to the reduction of systemic side effects and is obviously favorable for the improvement of a therapeutic effect. Considering a systemic drug, on the other hand, release in the colon is disadvantageous in that the colon is shorter and poorer in development of microvilli than the small intestine and therefore has a smaller surface area available for absorption and is less permeable to a polar compound. However, the average retention time in the ascending colon is about 3 hours in younger people and about 10 hours in older people (Hongo et al., NICHIHEIKATSUKINSHI, 24:55-60 (1988)), which is equal to or even longer than that in the small intestine (about 3 to 4 hours), and it means a long, effective absorption time. Considering the aspect of the colon as a site of administration of peptide or protein-based drugs, the colon is advantageous in that no digestive enzymes are secreted and that the peptidase activity of the membrane of the large intestine is lower than that of the small intestine (Kopecek et al., *Proc. Int. Symp. Control. Rel. Bioact. Mat.,* 17:130-131 (1990)). Therefore, drug release in the colon is expected to give improved systemic bioavailability.

A large number of preparations targeting the lower part of the gastrointestinal tract, especially the colon, have been reported. These systems are roughly divided into four types: (1) a delayed release system designed to release a drug in accordance with a change in pH; (2) a timed-release system designed to release a drug after a predetermined time; (3) a microflora enzyme system making use of the abundant enterobacteria in the lower part of the gastrointestinal tract; and (4) a system making use of a lectin-like substance specific to the large intestine.

The delayed release system uses an acrylic or cellulosic enteric coating material and dissolves on pH change. Because of ease of preparation, many reports on this system have been made. Taking the system using the acrylic enteric coating material Eudragit S as an example, many reports can be found, such as those by Behringer, Manchester University, Saale Co., and the like. However, the group from Manchester University reported at AAPS in 1993 that for such enterically-coated systems, the timing of drug release is determined by the transit of the system in the gastrointestinal tract rather than a pH change and, therefore, the specificity to the colon is low. Further, it is very likely that the other similar delayed release systems are also unsuccessful in colon-specific drug release.

The timed-release system is represented by the Time Erosion System (TES) from Fujisawa Pharmaceutical Co., Ltd. and Pulsincap from H. P. Scherer. According to these systems, the site of drug release is determined by the time of transit of the system in the gastrointestinal tract, which makes it difficult to target the release of a drug in the lower gastrointestinal tract. Since the transit of the system in the gastrointestinal tract is largely influenced by the gastric emptying time, some systems can be made with an enteric coating. Nevertheless, it is difficult to release a drug specifically in the colon, considering that the transit time of the system in the small intestine displays both intra- and inter-variation and also largely varies according to the disease or disorder to be treated.

Of particular interest is the system using the enterobacteria located in the lower gastrointestinal tract. This system is classified into three categories: (1) those utilizing degradation of azoaromatic polymers by an azo-reductase produced from enterobacteria as reported in Saffran et al., *Science,* 233:1081-1084 (1986) and Kopecek et al., *Pharmaceutical Research,* 9:1540-1545 (1992); (2) those utilizing degradation of polysaccharides by β-galactosidase of enterobacteria as reported in Japanese Patent Application No. 5-50863 and Bauer et al., *Pharmaceutical Research,* 10:5218 (1993); and (3) those utilizing degradation of chitosan by chitosanase as reported in Japanese Patent Application No. 4-217924 and Japanese Patent Application No. 4-225922. However, degradation of an azoaromatic polymer by enterobacteria is slow (Kopecek et al., supra) and may produce a harmful substance, making it unsuitable for long-term use. In fact, such a system containing insulin, when administered to beagle dogs, only achieved low efficacy (Saffran et al., *Biochemical Society Transactions,* 18:752-754 (1990)). The system using a polysaccharide is considered to cause no safety concerns because a material that has been taken as dietary fiber is used. However, according to a study performed by Cook et al., *Pharmaceutical Research,* 10:S223 (1993), the polysaccharide pectin is not only slowly degraded by enterobacteria, but the drug is released at a point in time prior to the arrival of the system in the colon. Therefore, this system appears to be ineffective as a colon-specific drug release system. Similarly, the drug release in artificial intestinal juice was found to be uncontrolled and non-specific (see, Japanese Patent Application No. 5-50863).

The system utilizing a lectin-like substance present in the large intestine has been reported in Kopecek et al., *Proc. Int. Symp. Control. Rel. Bioact. Mat.,* 17:130-131 (1990). This technique relates to a polymeric system prepared by binding fucose and a drug to a polymer via an azo bond, utilizing a lectin-like substance present in the large intestine for fucose recognition, and controlling the transit of the system in the colon so as to let the system release the drug by the action of an azo-reductase. However, the fucose-recognizing lectin is specific only to guinea pigs. Therefore, the technique cannot be applied directly to humans.

As a result, none of the various systems described above for colonic drug release is satisfactory for providing site-specific drug release to the colon.

Another disadvantage of the various systems described above is the lack of sufficient pharmacological effects of the drug in the second half of the day from a system taken only once daily, especially for drugs where prolonged and consistent efficacy is required for effective treatment of a disease or disorder. In particular, delivery systems containing drugs that are quickly eliminated from plasma or have site-specific absorption patterns are confronted with the difficulty of maintaining effective levels over the period of a full day following oral administration. In general, such systems necessitate a dosing regimen where a patient is administered the drug at least twice a day. However, the inconvenience associated with multiple daily administrations, especially among children, leads to patient non-compliance and results in the ineffective treatment of a disease or disorder. As such, none of the above-described systems is suitable for providing sustained, site-specific drug release.

Thus, there is a need to develop a drug delivery system for the release of a drug in the gastrointestinal tract that provides, for example: (1) long-lasting drug efficacy (e.g., sustained release for about 24 hours); (2) site-specific delivery to multiple release sites (e.g., drug release in both the small intestine and colon); (3) reduced dosing frequency; and (4) drug release that is independent of the transit time of the system through the gastrointestinal tract. The present invention satisfies these and other needs.

BRIEF SUMMARY OF THE INVENTION

The present invention provides novel compositions and methods for the multiple release of a drug in the gastrointestinal tract of a subject through the use of an oral multiple drug release system. The drug release system provides, for example, site-specific release of the drug to both the upper and lower gastrointestinal tract in the form of multiple controlled doses for long-lasting efficacy, thereby reducing the drug dosing frequency. The release of the drug can be sustained, pulsated, or a combination thereof.

As such, in one aspect, the present invention provides an oral multiple drug release composition, the composition comprising:
  (a) a drug core comprising a first drug and a saccharide;
  (b) an organic acid-soluble polymer, wherein the drug core is coated by the organic acid-soluble polymer;
  (c) a water-permeable, release-controlling polymer, wherein the organic acid-soluble polymer is coated by the water-permeable, release-controlling polymer; and
  (d) an enteric coat comprising a mixture of an enteric coating polymer and a second drug, wherein the water-permeable, release-controlling polymer is coated by the enteric coat, wherein the composition releases the second drug in the small intestine and the first drug in the colon.

In another aspect, the present invention provides an oral multiple drug release composition, the composition comprising:
  (a) a drug core comprising a first drug and a saccharide;
  (b) an organic acid-soluble polymer, wherein the drug core is coated by the organic acid-soluble polymer;
  (c) a drug layer comprising a second drug, wherein the organic acid-soluble polymer is coated by the drug layer;
  (d) a water-permeable, release-controlling polymer, wherein the drug layer is coated by the water-permeable, release-controlling polymer; and
  (e) an enteric coat comprising an enteric coating polymer, wherein the water-permeable, release-controlling polymer is coated by the enteric coat, wherein the composition releases the second drug in the small intestine and the first drug in the colon.

In yet another aspect, the present invention provides an oral multiple drug release composition, the composition comprising:
  (a) a drug core comprising a first drug;
  (b) a saccharide, wherein the drug core is coated by the saccharide;
  (c) an organic acid-soluble polymer, wherein the saccharide is coated by the organic acid-soluble polymer;
  (d) a water-permeable, release-controlling polymer, wherein the organic acid-soluble polymer is coated by the water-permeable, release-controlling polymer; and
  (e) an enteric coat comprising a mixture of an enteric coating polymer and a second drug, wherein the water-permeable, release-controlling polymer is coated by the enteric coat, wherein the composition releases the second drug in the small intestine and the first drug in the colon.

In still yet another aspect, the present invention provides an oral multiple drug release composition, the composition comprising:
  a first component, the first component comprising:
    (a) a drug core comprising a first drug;
    (b) a water-permeable, release-controlling polymer, wherein the drug core is coated by the water-permeable, release-controlling polymer; and
    (c) an enteric coat comprising an enteric coating polymer, wherein the water-permeable, release-controlling polymer is coated by the enteric coat; and
  a second component, the second component comprising:
    (a) a drug core comprising a second drug and a saccharide;
    (b) an organic acid-soluble polymer, wherein the drug core is coated by the organic acid-soluble polymer; and
    (c) an enteric coat comprising an enteric coating polymer, wherein the organic acid-soluble polymer is coated by the enteric coat, wherein the first component releases the first drug in the small intestine and the second component releases the second drug in the colon.

Without being bound to any particular theory, the compositions described above release the drug contained in the drug core in the colon through the production by enterobacteria of an organic acid from the saccharide that dissolves the organic acid-soluble polymer.

In a further aspect, the present invention provides a method for the multiple release of a drug in the gastrointestinal tract, the method comprising:
  orally administering to a subject a composition comprising:
    (a) a drug core comprising a first drug and a saccharide;
    (b) an organic acid-soluble polymer, wherein the drug core is coated by the organic acid-soluble polymer;
    (c) a water-permeable, release-controlling polymer, wherein the organic acid-soluble polymer is coated by the water-permeable, release-controlling polymer; and
    (d) an enteric coat comprising a mixture of an enteric coating polymer and a second drug, wherein the water-permeable, release-controlling polymer is coated by the enteric coat, wherein the composition releases the second drug in the small intestine and the first drug in the colon.

In another aspect, the present invention provides a method for the multiple release of a drug in the gastrointestinal tract, the method comprising:
  orally administering to a subject a composition comprising:
    (a) a drug core comprising a first drug and a saccharide;
    (b) an organic acid-soluble polymer, wherein the drug core is coated by the organic acid-soluble polymer;

(c) a drug layer comprising a second drug, wherein the organic acid-soluble polymer is coated by the drug layer;
(d) a water-permeable, release-controlling polymer, wherein the drug layer is coated by the water-permeable, release-controlling polymer; and
(e) an enteric coat comprising an enteric coating polymer, wherein the water-permeable, release-controlling polymer is coated by the enteric coat, wherein the composition releases the second drug in the small intestine and the first drug in the colon.

In yet another aspect, the present invention provides a method for the multiple release of a drug in the gastrointestinal tract, the method comprising:
orally administering to a subject a composition comprising:
(a) a drug core comprising a first drug;
(b) a saccharide, wherein the drug core is coated by the saccharide;
(c) an organic acid-soluble polymer, wherein the saccharide is coated by the organic acid-soluble polymer;
(d) a water-permeable, release-controlling polymer, wherein the organic acid-soluble polymer is coated by the water-permeable, release-controlling polymer; and
(e) an enteric coat comprising a mixture of an enteric coating polymer and a second drug, wherein the water-permeable, release-controlling polymer is coated by the enteric coat, wherein the composition releases the second drug in the small intestine and the first drug in the colon.

In still yet another aspect, the present invention provides a method for the multiple release of a drug in the gastrointestinal tract, the method comprising:
orally administering to a subject a composition comprising:
a first component, the first component comprising:
(a) a drug core comprising a first drug;
(b) a water-permeable, release-controlling polymer, wherein the drug core is coated by the water-permeable, release-controlling polymer; and
(c) an enteric coat comprising an enteric coating polymer, wherein the water-permeable, release-controlling polymer is coated by the enteric coat; and
a second component, the second component comprising:
(a) a drug core comprising a second drug and a saccharide;
(b) an organic acid-soluble polymer, wherein the drug core is coated by the organic acid-soluble polymer; and
(c) an enteric coat comprising an enteric coating polymer, wherein the organic acid-soluble polymer is coated by the enteric coat, wherein the first component releases the first drug in the small intestine and the second component releases the second drug in the colon.

In a further aspect, the present invention provides a method for providing a multiple drug release profile in a subject, the method comprising:
administering to the subject an oral drug formulation comprising:
(a) a first drug, wherein the first drug is released in the small intestine from about 0.5 hours to about 2 hours following administration; and
(b) a second drug, wherein the second drug is released in the colon from about 6 hours to about 12 hours following administration.

Other objects, features, and advantages of the present invention will be apparent to one of skill in the art from the following detailed description and figures.

DETAILED DESCRIPTION OF THE INVENTION

I. Definitions

Figure 1:
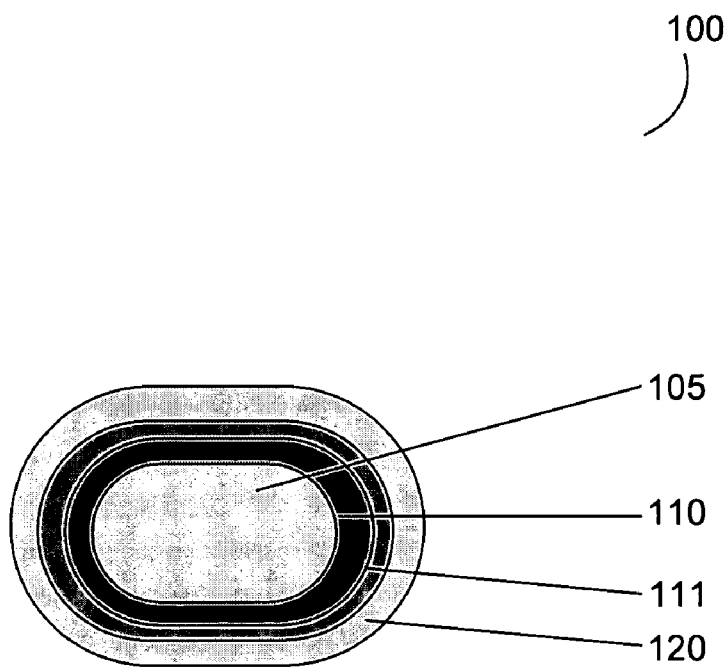
FIG. 1 shows a diagram of a multiple release tablet of the present invention.

As used herein, the following terms have the meanings ascribed to them unless specified otherwise.

The terms "system" and "composition" are used interchangeably herein to refer to an oral multiple drug release composition of the present invention.

The term "lower gastrointestinal tract" refers to the part of the gastrointestinal tract from the ileum to the colon. The term "colon" refers to the part of the large intestine from the cecum to the rectum. The term "cecum" refers to a cecal pouch at the beginning of the large intestine into which the ileum opens from one side and which is continuous with the colon. The term "upper gastrointestinal tract" refers to the part of the gastrointestinal tract from the stomach to the jejunum. The term "small intestine" refers to the part of the intestine that lies between the stomach and colon, and consists of the duodenum, jejunum, and ileum.

The term "multiple drug release system" or "multiple drug release composition" refers to either a multiple-pulsated drug release system wherein the drug is released as pulses at multiple sites in the gastrointestinal tract (e.g., stomach, small intestine, and colon) or a sustained drug release system wherein the continued release of drug occurs at multiple sites in the gastrointestinal tract as the system transits through the gastrointestinal tract and lasts for a period of from about 0.5 hours to about 24 hours. The term "multiple release" or "multiple drug release" refers to either the multiple-pulsated drug release or the sustained drug release that is provided by a multiple drug release system.

The term "drug core" refers to the innermost layer of the multiple release system of the present invention and comprises one of the following: (1) a first drug; (2) a mixture of a first drug and a saccharide; or (3) a first drug and a saccharide, wherein the first drug is coated by the saccharide. Optionally, the drug core can be coated by a water-permeable, release-controlling polymer such as HPMC. Optionally, the drug core can contain a buffering agent.

II. General Overview

The present invention provides novel compositions and methods for the multiple release of a drug in the gastrointestinal tract of a subject through the use of an oral multiple drug release system. The drug release system provides, for example, site-specific release of the drug to both the upper and lower gastrointestinal tract in the form of multiple controlled doses for long-lasting efficacy, thereby reducing the drug dosing frequency. In certain aspects, the drug release can be sustained release, pulsated release, or a combination of sustained release and pulsated release.

In particular, for drugs with either short or long local and/or pharmacological activity after administration, the systems of the present invention provide the advantage of delivering the drug to more than one specific site in the gastrointestinal tract. As such, the multiple release of the drug facilitates its site-specific absorption and maintains its efficacy such as for example for a prolonged period of time (e.g., about 24 hours), resulting in the use of less amounts of the drug. Further, the site-specific release of the drug permits the delivery of a high concentration of the drug to multiple sites in the gastrointestinal tract where it can be efficiently absorbed while avoiding unfavorable side-effects.

The systems of the present invention exploit the advantages of a colon-specific drug delivery system, which for example utilize the colonic enterobacteria and their corresponding enzymatic activities, and incorporate additional drug layers for multiple release at specific sites in the gastrointestinal tract. As such, the systems provide the release of drug, first in the small intestine, and then in the colon. The first drug release in the small intestine establishes an effective level of drug, while the second drug release in the colon maintains the effective level of drug for about 24 hours following administration. Since the degradation of polysaccharides by enterobacteria occurs only in the colon, this assures that the dissolution of the organic acid-soluble polymer and the second drug release only occurs once the system has reached the colon.

The drug release patterns in the present invention can be designed either as a pulsated release, sustained release, or combinations thereof. The actual design of any particular drug will depend in-part on the pharmacodynamic (i.e., duration of activity) and/or the pharmacokinetic (i.e., elimination half-life from plasma) relationship of the particular drug. For example, in the case of a drug requiring a 24-hour efficacy in its pharmacological effect, the drug would be beneficial and advantageous to the patient if the design and delivery of such drug is sustained-release. A drug such as acyclovir with a biological half-life of 2.5 hours would be a good candidate, for instance, to be a sustained-release dose compared to its current 5 times per day dose. Preferred candidates for pulsated-release can be, for instance, an ion channel blocker (e.g., omeprazole) or a $H_2$ receptor inhibitor (e.g., famotidine), which have short biological half-lives but a long duration in their pharmacological action. Such drugs would be better designed in a multiple pulsated release formulation to maximize their pharmacological effects.

III. Description of the Embodiments

FIG. 1 shows a diagram of the multiple release system 100 of the present invention. This diagram is merely an illustration and should not limit the scope of the claims herein. One of ordinary skill in the art will recognize other variations, modifications, and alternatives.

In one aspect, with reference to FIG. 1, the present invention provides an oral drug delivery system 100. Preferably, the drug delivery system provides for the multiple release of a drug in the gastrointestinal tract. In one embodiment, the system 100 comprises a drug core 105, which includes a mixture of a first drug 106 and a saccharide 107, such as lactulose. The system 100 includes an organic acid-soluble polymer 110, wherein the drug core 105 is coated by the organic acid-soluble polymer 110. In this embodiment, the system 100 includes a water-permeable, release-controlling polymer 111, wherein the organic acid-soluble polymer 110 is coated by the water-permeable, release-controlling polymer 111. The system 100 further includes an enteric coat 120. The enteric coat 120 comprises a mixture of an enteric coating polymer 122 and a second drug 125, wherein the water-permeable, release-controlling polymer 111 is coated by the enteric coat 120. In operation, the system 100 releases the second drug 125 contained in the enteric coat 120 in the small intestine and then releases the first drug 106 contained in the drug core 105 in the colon through the production by enterobacteria of an organic acid from the saccharide 107 that dissolves the organic acid-soluble polymer 110.

In an alternative embodiment, the system 100 comprises a drug core 105 including a first drug 106 and a saccharide 107, wherein the first drug 106 is coated by a saccharide 107. Optionally, a water-permeable, release-controlling polymer can be included in the drug core 105 as a layer in-between the first drug 106 and the saccharide 107 to, e.g., permit the sustained release of the first drug 106 and/or to prevent any interaction between the first drug 106 and the saccharide 107. This drug core 105 is then coated by the organic acid-soluble polymer 110, followed by the water-permeable, release-controlling polymer 111, and then the enteric coat 120. Alternatively, a water-permeable, release-controlling polymer can be admixed with the first drug 106, and, optionally, coated by the same or different water-permeable, release-controlling polymer.

In certain instances, the first drug 106 and the second drug 125 are either the same drug or are different drugs. In certain other instances, the first drug 106 and/or the second drug 125 is a combination of at least two drugs. In one embodiment, the first drug 106 and the second drug 125 are independently selected from the group consisting of a proton pump inhibitor, a peptide, a protein, a hormone, an anti-inflammatory agent, an antitussive expectorant, a vasodilator, an analgesic, a histamine $H_2$-receptor antagonist, an antibiotic, an antiepileptic agent, an antigout agent, an antitumor agent, an antidiabetic agent, an antipsychotic agent, a prostatomegaly agent, an antiasthma agent, a drug with a short pharmacokinetic half-life, pharmaceutically acceptable salts thereof, derivatives thereof, and combinations thereof. Preferably, the drug is a proton pump inhibitor. Suitable proton pump inhibitors include, without limitation, omeprazole, esomeprazole, lansoprazole, rabeprazole, pantoprazole, pharmaceutically acceptable salts thereof, derivatives thereof, and combinations thereof. In an additional embodiment, the drug core 105 and/or the enteric coat 120 further comprise a buffering agent. With proton pump inhibitors, the pulsated release pattern is preferred.

In another embodiment, the saccharide 107 is selected from the group consisting of lactulose, raffinose, cellobiose, stachyose, fructoligosaccharide, sucrose, glucose, xylose, fructose, mannitol, maltose, galactose, and combinations thereof. In a preferred embodiment, the saccharide 107 is lactulose. In certain instances, the saccharide 107 is present in an amount of from about 10% to about 90% w/w. In yet another embodiment, the organic acid-soluble polymer 110 is selected from the group consisting of a dimethylaminoethyl methacrylate-methyl methacrylate copolymer, a polyvinyl acetal diethylaminoacetate, chitosan, and combinations thereof. Preferably, the dimethylaminoethyl methacrylate-methyl methacrylate copolymer is a dimethylaminoethyl methacrylate-methyl methacrylate-butyl methacrylate copolymer (e.g., Eudragit E). In certain instances, the organic acid-soluble polymer 110 is present in an amount of from about 2.5% to about 40.0% w/w. In a preferred embodiment, the organic acid-soluble polymer 110 dissolves at a pH lower than about 6.

In still yet another embodiment, the water-permeable, release-controlling polymer 111 is selected from the group consisting of a copolymer of ethyl acrylate, methyl methyacrylate, and trimethylammonioethyl methacrylate chloride, ethyl cellulose, hydroxypropylmethylcellulose(HPMC), hydroxypropylcellulose, polyethylene oxide, polyvinylpyrrolidone, and combinations thereof. In a preferred embodiment, the water-permeable, release-controlling polymer 111 is HPMC. In a further embodiment, the enteric coating polymer 122 is selected from the group consisting of a methyl methacrylate-methylacrylate acid (1:1) copolymer, a methyl methacrylate-methacrylate acid (2:1) copolymer, an ethyl acrylate-methacrylic acid (1:1) copolymer, hydroxypropylmethylcellulose phthalate, cellulose acetate phthalate, shellac, and combinations thereof.

In certain instances, the system 100 further comprises an outer drug coat having a third drug, wherein the enteric coat 120 is coated by the outer drug coat and the system 100 releases the third drug contained in the outer drug coat in the stomach. In one embodiment, the outer drug coat further comprises a buffering agent. In a preferred embodiment, the system 100 is in the form of a tablet or granule.

In a particularly preferred embodiment, the present invention provides an oral drug delivery system 100, wherein the drug core comprises a mixture of a first proton pump inhibitor and lactulose, the organic acid-soluble polymer is a dimethylaminoethyl methacrylate-methyl methacrylate-butyl methacrylate copolymer, the water-permeable, release-controlling polymer is HPMC, and the enteric coat comprises a mixture of an enteric coating polymer and a second proton pump inhibitor.

Figure 2:
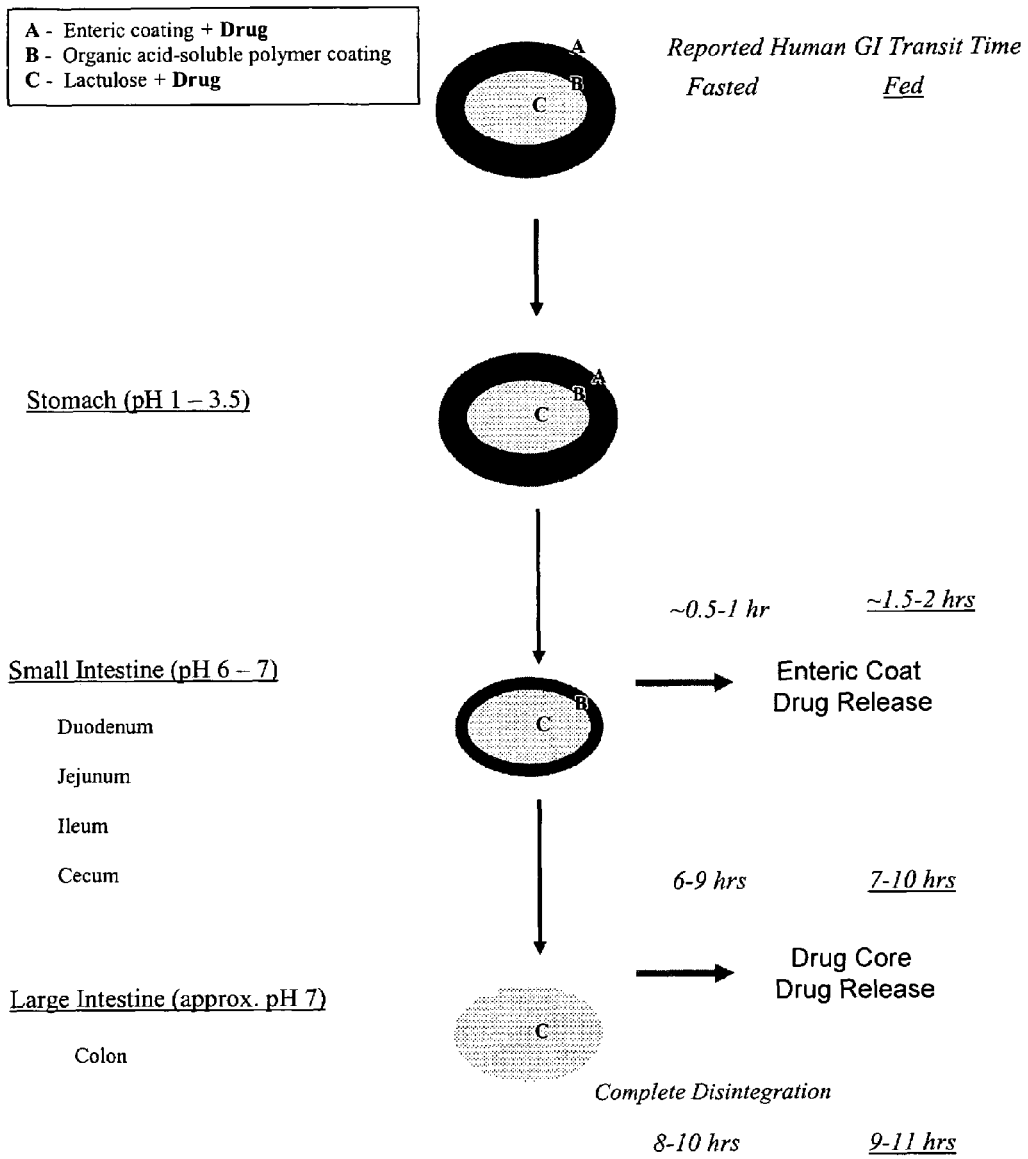
FIG. 2 shows a diagram of a multiple drug release system of the present invention as the system passes through the gastrointestinal tract.

FIG. 2 shows a diagram of a particular embodiment of the multiple drug release system of the present invention as the system passes through the gastrointestinal tract. In this diagram, the system comprises a drug core (C), which includes a first drug and the saccharide lactulose. An organic acid-soluble polymer (B) coats the drug core, and an enteric coat (A) comprising an enteric coating polymer and a second drug coats the organic acid-soluble polymer. The enteric coat protects the system as it transits through the acidic (i.e., pH 1-3.5) environment of the stomach. However, upon reaching the less acidic (i.e., pH 6-7) environment of the small intestine, the enteric coat dissolves, thereby releasing the second drug into the small intestine. In fasted humans, this initial release of drug occurs at about 0.5 to about 1 hour after administration. In fed humans, this initial release of drug occurs at about 1.5 to about 2 hours after administration.

Following the dissolution of the enteric coat and the initial release of drug, the system continues through the small intestine and into the colon. During this transit, the organic acid-soluble polymer, which dissolves at a pH lower than about 6, swells and allows enough water to permeate into the drug core to dissolve the saccharide present therein. The dissolved saccharide diffuses through the organic acid-soluble polymer into the lumen of the colon, where it is now accessible to enterobacteria. The enterobacteria then enzymatically degrade the saccharide into an organic acid, thereby lowering the pH of that area of the colon to a pH lower than about 6. The lowered pH surrounding the system dissolves the organic acid-soluble polymer and releases the first drug contained in the drug core in the colon. In fasted humans, this subsequent release of drug occurs at about 6 to about 9 hours after administration. In fed humans, this subsequent release of drug occurs at about 7 to about 10 hours after administration. Complete disintegration of the drug core occurs within the colon at about 8 to about 10 hours after administration in fasted humans and about 9 to about 11 hours after administration in fed humans. Therefore, as the timing of drug release in the gastrointestinal tract varies depending on whether a subject has consumed food, the drug release profile can be changed by fasting or feeding the subject prior to system administration.

As such, the system shown in FIG. 2 provides an immediate site-specific release of drug in the small intestine and a later site-specific release of drug in the colon. While the initial release of drug in the small intestine provides an effective, therapeutic level of drug, the subsequent pulse of drug in the colon maintains and can sustain an effective drug level for up to about 24 hours after administration. Such drug delivery systems permit a more controlled and consistent pharmacological effect for drugs for a longer duration, without unwanted side-effects. In particular, the multiple release systems of the present invention provide for the long-lasting efficacy of drugs such as proton pump inhibitors, whose pharmacological effects decline significantly after half a day following their administration.

Figure 3:
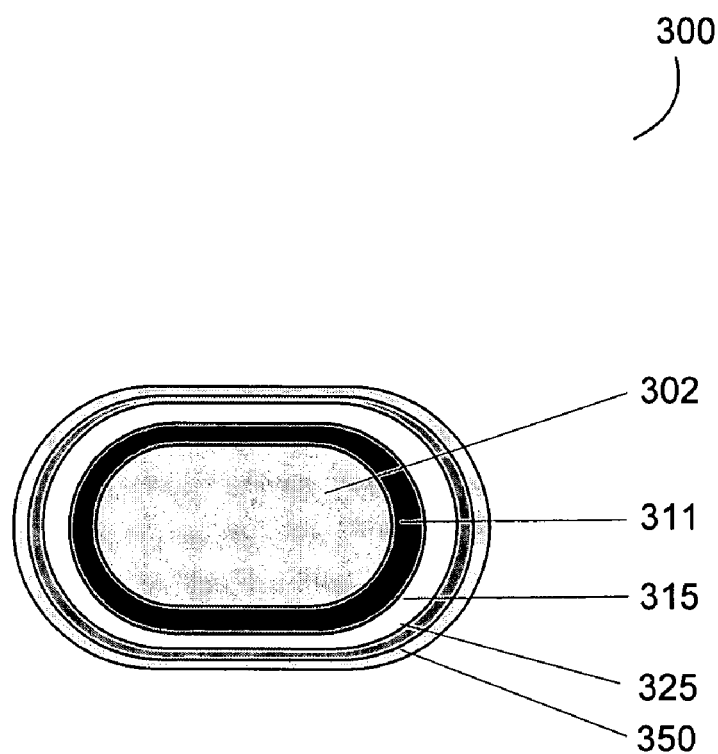
FIG. 3 shows a diagram of a multiple release tablet of the present invention which contains a separate drug layer.

FIG. 3 shows a diagram of the multiple release system 300 of the present invention. This diagram is merely an illustration and should not limit the scope of the claims herein. One of ordinary skill in the art will recognize other variations, modifications, and alternatives.

In another aspect, with reference to FIG. 3, the present invention provides an oral drug delivery system 300. Preferably, the drug delivery system provides for the multiple release of a drug in the gastrointestinal tract. The system 300 includes a drug core 302 comprising a first drug 304 and a saccharide 310. The system 300 also includes an organic acid-soluble polymer 311, wherein the drug core 302 is coated by the organic acid-soluble polymer 311. The system 300 further includes a drug layer 315 comprising a second drug 317, wherein the organic acid-soluble polymer 311 is coated by the drug layer 315. In addition, the system 300 includes a water-permeable, release-controlling polymer 325, wherein the drug layer 315 is coated by the water-permeable, release-controlling polymer 325. The system 300 further includes an enteric coat 350 comprising an enteric coating polymer 355, wherein the water-permeable, release-controlling polymer 325 is coated by the enteric coat 350. In operation, the system 300 releases the second drug 317 contained in the drug layer 315 in the small intestine and then releases the first drug 304 contained in the drug core 302 in the colon through the production by enterobacteria of an organic acid from the saccharide 310 that dissolves the organic acid-soluble polymer 311.

In an alternative embodiment, the system 300 comprises a drug core 302 including a first drug 304 and a saccharide 310, wherein the first drug 304 is coated by a saccharide 310. Optionally, a water-permeable, release-controlling polymer can be included in the drug core 302 as a layer in-between the first drug 304 and the saccharide 310 to, e.g., permit the sustained release of the first drug 304 and/or to prevent any interaction between the first drug 304 and the saccharide 310. This drug core 302 is then coated by the organic acid-soluble polymer 311, followed by the drug layer 315, then the water-permeable, release-controlling polymer 325, and then the enteric coat 350. Alternatively, a water-permeable, release-controlling polymer can be admixed with the first drug 304, and, optionally, coated by the same or different water-permeable, release-controlling polymer.

In certain instances, the first drug 304 and the second drug 317 are either the same drug or are different drugs. In certain other instances, the first drug 304 and/or the second drug 317 is a combination of at least two drugs. In one embodiment, the first drug 304 and the second drug 317 are independently selected from the group consisting of a proton pump inhibitor, a peptide, a protein, a hormone, an anti-inflammatory agent, an antitussive expectorant, a vasodilator, an analgesic, a histamine $H_2$-receptor antagonist, an antibiotic, an antiepileptic agent, an antigout agent, an antitumor agent, an antidiabetic agent, an antipsychotic agent, a prostatomegaly agent, an antiasthma agent, a drug with a short pharmacokinetic half-life, pharmaceutically acceptable salts thereof, derivatives thereof, and combinations thereof. Preferably, the drug is a proton pump inhibitor including, without limitation, omeprazole, esomeprazole, lansoprazole, rabeprazole, pantoprazole, pharmaceutically acceptable salts thereof, derivatives thereof, and combinations thereof. In an additional embodiment, the drug core 302 and/or the drug layer 315 further comprise a buffering agent.

In another embodiment, the saccharide 310 is selected from the group consisting of lactulose, raffinose, cellobiose, stachyose, fructoligosaccharide, sucrose, glucose, xylose, fructose, mannitol, maltose, galactose, and combinations thereof. In a preferred embodiment, the saccharide 310 is lactulose. In certain instances, the saccharide 310 is present in an amount of from about 10% to about 90% w/w. In yet another embodiment, the organic acid-soluble polymer 311 is selected from the group consisting of a dimethylaminoethyl methacrylate-methyl methacrylate copolymer, a polyvinyl acetal diethylaminoacetate, chitosan, and combinations thereof. Preferably, the dimethylaminoethyl methacrylate-methyl methacrylate copolymer is a dimethylaminoethyl methacrylate-methyl methacrylate-butyl methacrylate copolymer (e.g., Eudragit E). In certain instances, the organic acid-soluble polymer 311 is present in an amount of from about 2.5% to about 40.0% w/w. In a preferred embodiment, the organic acid-soluble polymer 311 dissolves at a pH lower than about 6.

In still yet another embodiment, the water-permeable, release-controlling polymer 325 is selected from the group consisting of a copolymer of ethyl acrylate, methyl methyacrylate, and trimethylammonioethyl methacrylate chloride, ethyl cellulose, hydroxypropylmethylcellulose (HPMC), hydroxypropylcellulose, polyethylene oxide, polyvinylpyrrolidone, and combinations thereof. In a preferred embodiment, the water-permeable, release-controlling polymer 325 is HPMC. In a further embodiment, the enteric coating polymer 355 is selected from the group consisting of a methyl methacrylate-methylacrylate acid (1:1) copolymer, a methyl methacrylate-methacrylate acid (2:1) copolymer, an ethyl acrylate-methacrylic acid (1:1) copolymer, hydroxypropylmethylcellulose phthalate, cellulose acetate phthalate, shellac, and combinations thereof.

In certain instances, the enteric coat 350 comprises a mixture of the enteric coating polymer 355 and a third drug. In an additional embodiment, the enteric coat 350 further comprises a buffering agent. In an alternative embodiment, the system 300 further comprises an outer drug coat having a third drug, wherein the enteric coat 350 is coated by the outer drug coat and the system 300 releases the third drug contained in the outer drug coat in the stomach. In a further embodiment, the outer drug coat further comprises a buffering agent. In a preferred embodiment, the system 300 is in the form of a tablet or granule.

In a particularly preferred embodiment, the present invention provides an oral drug delivery system 300, wherein the drug core comprises a mixture of a first proton pump inhibitor and lactulose, the organic acid-soluble polymer is a dimethylaminoethyl methacrylate-methyl methacrylate-butyl methacrylate copolymer, the drug layer comprises a second proton pump inhibitor, the water-permeable, release-controlling polymer is HPMC, and the enteric coat comprises an enteric coating polymer.

Figure 4:
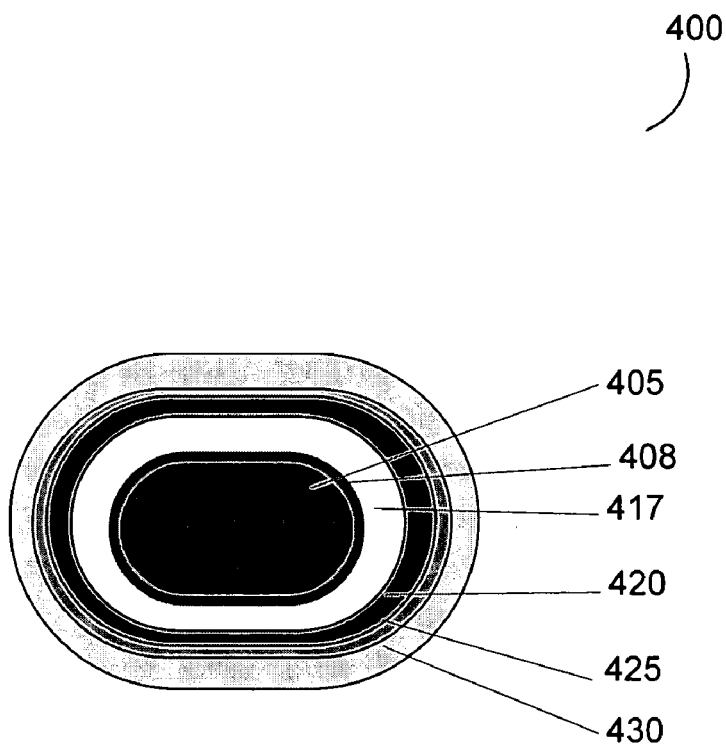
FIG. 4 shows a diagram of a multiple release tablet of the present invention comprising a compressed saccharide layer.

FIG. 4 shows a diagram of the multiple release system 400 of the present invention. This diagram is merely an illustration and should not limit the scope of the claims herein. One of ordinary skill in the art will recognize other variations, modifications, and alternatives.

In yet another aspect, with reference to FIG. 4, the present invention provides an oral drug delivery system 400. Preferably, the drug delivery system provides for the multiple release of a drug in the gastrointestinal tract. In one embodiment, the system 400 comprises a drug core 405, which includes a first drug 406 coated by a water-permeable, release-controlling polymer 408, and further coated by a saccharide 417, such as lactulose, using a compressed coating manufacturing process. The system 400 also includes an organic acid-soluble polymer 420, wherein the drug core 405 is coated by the organic acid-soluble polymer 420. The system 400 further includes a water-permeable, release-controlling polymer 425, wherein the organic acid-soluble polymer 420 is coated by the water-permeable, release-controlling polymer 425. In addition, the system 400 includes an enteric coat 430. The enteric coat 430 comprises a mixture of an enteric coating polymer 432 and a second drug 435, wherein the water-permeable, release-controlling polymer 425 is coated by the enteric coat 430. In operation, the system 400 releases the second drug 435 contained in the enteric coat 430 in the small intestine and then releases the first drug 406 contained in the drug core 405 in the colon through the production by enterobacteria of an organic acid from the saccharide 417 that dissolves the organic acid-soluble polymer 420.

In certain instances, the first drug 406 and the second drug 435 are either the same drug or are different drugs. In certain other instances, the first drug 406 and/or the second drug 435 is a combination of at least two drugs. In one embodiment, the first drug 406 and the second drug 435 are independently selected from the group consisting of a proton pump inhibitor, a peptide, a protein, a hormone, an anti-inflammatory agent, an antitussive expectorant, a vasodilator, an analgesic, a histamine $H_2$-receptor antagonist, an antibiotic, an antiepileptic agent, an antigout agent, an antitumor agent, an antidiabetic agent, an antipsychotic agent, a prostatomegaly agent, an antiasthma agent, a drug with a short pharmacokinetic half-life, pharmaceutically acceptable salts thereof, derivatives thereof, and combinations thereof. Preferably, the drug is a proton pump inhibitor such as, for example, omeprazole, esomeprazole, lansoprazole, rabeprazole, pantoprazole, pharmaceutically acceptable salts thereof, derivatives thereof, and combinations thereof. In an additional embodiment, the drug core 405 and/or the enteric coat 430 further comprise a buffering agent.

In another embodiment, the saccharide 417 is selected from the group consisting of lactulose, raffinose, cellobiose, stachyose, fructoligosaccharide, sucrose, glucose, xylose, fructose, mannitol, maltose, galactose, and combinations thereof. In a preferred embodiment, the saccharide 417 is lactulose. In certain instances, the saccharide 417 is present in an amount of from about 10% to about 90% w/w. In yet another embodiment, the organic acid-soluble polymer 420 is selected from the group consisting of a dimethylaminoethyl methacrylate-methyl methacrylate copolymer, a polyvinyl acetal diethylaminoacetate, chitosan, and combinations thereof. Preferably, the dimethylaminoethyl methacrylate-methyl methacrylate copolymer is a dimethylaminoethyl methacrylate-methyl methacrylate-butyl methacrylate copolymer (e.g., Eudragit E). In certain instances, the organic acid-soluble polymer 420 is present in an amount of from about 2.5% to about 40.0% w/w. In a preferred embodiment, the organic acid-soluble polymer 420 dissolves at a pH lower than about 6.

In still yet another embodiment, the water-permeable, release-controlling polymers 408 and/or 425 are selected from the group consisting of a copolymer of ethyl acrylate, methyl methyacrylate, and trimethylammonioethyl methacrylate chloride, ethyl cellulose, hydroxypropylmethylcellulose (HPMC), hydroxypropylcellulose, polyethylene oxide, polyvinylpyrrolidone, and combinations thereof. Preferably, the water-permeable, release-controlling polymer 408 and/or 425 is HPMC. In a further embodiment, the enteric coating polymer 432 is selected from the group consisting of a methyl methacrylate-methylacrylate acid (1:1) copolymer, a methyl methacrylate-methacrylate acid (2:1) copolymer, an ethyl acrylate-methacrylic acid (1:1) copolymer, hydroxypropylmethylcellulose phthalate, cellulose acetate phthalate, shellac, and combinations thereof.

In certain instances, the system 400 further comprises an outer drug coat having a third drug, wherein the enteric coat 430 is coated by the outer drug coat and the system 400 releases the third drug contained in the outer drug coat in the stomach. In an additional embodiment, the outer drug coat further comprises a buffering agent. In a preferred embodiment, the system 400 is in the form of a tablet or granule.

Figure 5:
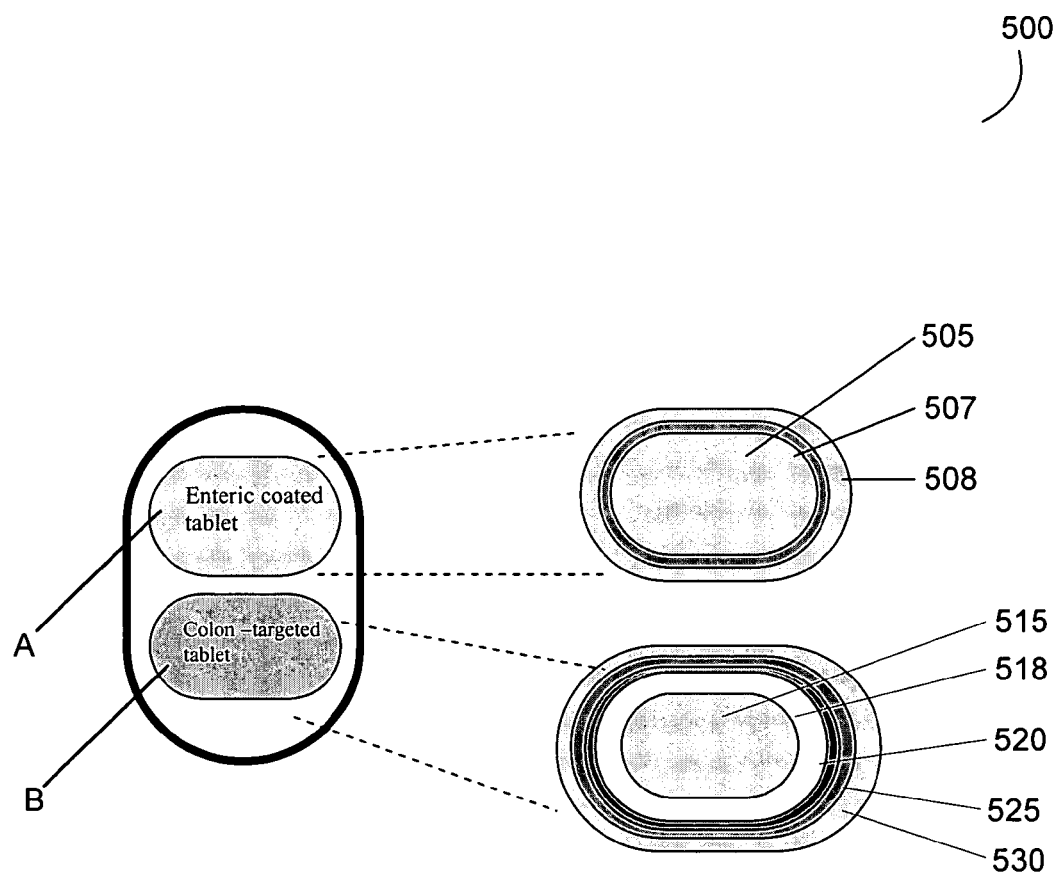
FIG. 5 shows a diagram of a capsule of the present invention which contains an enteric coated tablet and a colon-targeted tablet.

FIG. 5 shows a diagram of the multiple release system 500 of the present invention. This diagram is merely an illustration and should not limit the scope of the claims herein. One of ordinary skill in the art will recognize other variations, modifications, and alternatives.

In still yet another aspect, with reference to FIG. 5, the present invention provides an oral drug delivery system 500. Preferably, the drug delivery system provides for the multiple release of a drug in the gastrointestinal tract. The system 500 has two components: a first component A (i.e., enteric coated tablet) and a second component B (i.e., colon-targeted tablet). In one embodiment, the first component A comprises a drug core 505, which includes a first drug 506. The drug core 505 is coated by a water-permeable, release-controlling polymer 507. The first component A also includes an enteric coat 508 comprising an enteric coating polymer 509, wherein the water-permeable, release-controlling polymer 507 is coated by the enteric coat 508.

In another embodiment, the second component B comprises a drug core 515, which includes a second drug 516 and a saccharide 518, such as lactulose, wherein the second drug 516 is coated by the saccharide 518 using a compressed coating manufacturing process. Optionally, a water-permeable, release-controlling polymer is included in the drug core 515 as a layer in-between the second drug 516 and the saccharide 518. In an alternative embodiment, the drug core 515 comprises a mixture of the second drug 516 and the saccharide 518. The second component B also includes an organic acid-soluble polymer 520, wherein the saccharide 518 is coated by the organic acid-soluble polymer 520. The second component B further includes a water-permeable, release-controlling polymer 525, wherein the organic acid-soluble polymer 520 is coated by the water-permeable, release-controlling polymer 525. In addition, the second component B includes an enteric coat 530. The enteric coat 530 comprises an enteric coating polymer 532, wherein the water-permeable, release-controlling polymer 525 is coated by the enteric coat 530. In operation, the system 500 releases the first drug 506 contained in the drug core 505 of the first component A in the small intestine and then releases the second drug 516 contained in the drug core 515 of the second component B in the colon through the production by enterobacteria of an organic acid from the saccharide 518 that dissolves the organic acid-soluble polymer 520. In a preferred embodiment, the first and second components are inside a capsule.

In certain instances, the first drug 506 and the second drug 516 are either the same drug or are different drugs. In certain other instances, the first drug 506 and/or the second drug 516 is a combination of at least two drugs. In one embodiment, the first drug 506 and the second drug 516 are independently selected from the group consisting of a proton pump inhibitor, a peptide, a protein, a hormone, an anti-inflammatory agent, an antitussive expectorant, a vasodilator, an analgesic, a histamine $H_2$-receptor antagonist, an antibiotic, an antiepileptic agent, an antigout agent, an antitumor agent, an antidiabetic agent, an antipsychotic agent, a prostatomegaly agent, an antiasthma agent, a drug with a short pharmacokinetic half-life, pharmaceutically acceptable salts thereof, derivatives thereof, and combinations thereof. Preferably, the drug is a proton pump inhibitor. Suitable proton pump inhibitors include, without limitation, omeprazole, esomeprazole, lansoprazole, rabeprazole, pantoprazole, pharmaceutically acceptable salts thereof, derivatives thereof, and combinations thereof. In an additional embodiment, the drug core 505 of the first component A and/or the drug core 515 of the second component B further comprise a buffering agent.

In another embodiment, the saccharide 518 is selected from the group consisting of lactulose, raffinose, cellobiose, stachyose, fructoligosaccharide, sucrose, glucose, xylose, fructose, mannitol, maltose, galactose, and combinations thereof. In a preferred embodiment, the saccharide 518 is lactulose. In certain instances, the saccharide 518 is present in an amount of from about 10% to about 90% w/w. In yet another embodiment, the organic acid-soluble polymer 520 is selected from the group consisting of a dimethylaminoethyl methacrylate-methyl methacrylate copolymer, a polyvinyl acetal diethylaminoacetate, chitosan, and combinations thereof. Preferably, the dimethylaminoethyl methacrylate-methyl methacrylate copolymer is a dimethylaminoethyl methacrylate-methyl methacrylate-butyl methacrylate copolymer (e.g., Eudragit E). In a further embodiment, the organic acid-soluble polymer 520 is present in an amount of from about 2.5% to about 40.0% w/w. In a preferred embodiment, the organic acid-soluble polymer 520 dissolves at a pH lower than about 6.

In yet another embodiment, the water-permeable, release-controlling polymers 507 and/or 525 are selected from the group consisting of a copolymer of ethyl acrylate, methyl methyacrylate, and trimethylammonioethyl methacrylate chloride, ethyl cellulose, hydroxypropylmethylcellulose (HPMC), hydroxypropylcellulose, polyethylene oxide, polyvinylpyrrolidone, and combinations thereof. In a preferred embodiment, the water-permeable, release-controlling polymer 507 and/or 525 is HPMC. In a further embodiment, the enteric coating polymers 508 and/or 530 are selected from the group consisting of a methyl methacrylate-methylacrylate acid (1:1) copolymer, a methyl methacrylate-methacrylate acid (2:1) copolymer, an ethyl acrylate-methacrylic acid (1:1) copolymer, hydroxypropylmethylcellulose phthalate, cellulose acetate phthalate, shellac, and combinations thereof.

In certain instances, the enteric coat 530 in the second component B comprises a mixture of the enteric coating polymer 532 and a third drug. In an additional embodiment, the enteric coat 530 further comprises a buffering agent. In an alternative embodiment, the first component A, the second component B, or the combination thereof further comprises an outer drug coat having a third drug, wherein the enteric coats 508 and/or 530 are further coated by the outer drug coat and the system 500 releases the third drug contained in the outer drug coat in the stomach. In another embodiment, the outer drug coat further comprises a buffering agent.

In further aspects, the present invention provides methods for the multiple release of drugs in the gastrointestinal tract by orally administering to a subject any of the above-described multiple release systems. Preferably, the first drug and the second drug are the same drug and the concentration of the first drug and the second drug in the plasma is sustained for a period of about 24 hours following administration.

In another aspect, the present invention provides a method for providing a multiple drug release profile in a subject, the method comprising:
  administering to the patient an oral drug formulation comprising:
    (a) a first drug, wherein the first drug is released in the small intestine from about 0.5 hours to about 2 hours following administration; and
    (b) a second drug, wherein the second drug is released in the colon from about 6 hours to about 12 hours following administration.

IV. Multiple Drug Release Systems

The oral drug delivery systems of the present invention are comprised of the following elements: at least one drug, a saccharide, an organic acid-soluble polymer, a water-permeable, release-controlling polymer, and an enteric coat. Each of these elements will be described in greater detail below.

A. Drugs

Any drug having a pharmaceutical, pharmacological, or therapeutic effect is suitable for use in the systems of the present invention. Representative drugs include, but are not limited to, proton pump inhibitors, peptides, proteins, hormones, anti-inflammatory agents, antitussive expectorants, vasodilators, analgesics, histamine $H_2$-receptor antagonists, antibiotics, antiepileptic agents, antigout agents, antitumor agents, antidiabetic agents, antipsychotic agents, prostatomegaly agents, antiasthma agents, drugs with short pharmacokinetic half-lives, pharmaceutically acceptable salts thereof, derivatives thereof, and combinations thereof. In addition to these drugs, other active agents that are efficiently absorbed by both the upper and lower gastrointestinal tract are suitable for use in the present invention.

Suitable proton pump inhibitors include, without limitation, omeprazole, esomeprazole, lansoprazole, rabeprazole, pantoprazole, pharmaceutically acceptable salts thereof, derivatives thereof, and combinations thereof. With proton pump inhibitors, the pulsated release pattern is preferred.

Suitable peptides, proteins, and hormnones include, without limitation, insulin, calcitonin, angiotensin, vasopressin, desmopressin, LH-RH (luteinizing hormone-releasing hormone), somatostatin, glucagon, oxytocin, gastrin, ciclosporin, somatomedin, secretin, h-ANP (human artial natriuretic peptide), ACTH (adrenocorticotropic hormone), MSH (melanocyte-stimulating hormone), β-endorphin, muramyl dipeptide, enkephalin, neurotensin, bombesin, VIP (vasoactive intestinal polypeptide), CCK-8 (cholecystokinin-8), PTH (parathyroid hormone), CGRP (calcitonin gene-related peptide), TRH (thyrotropin-releasing hormone), endocerine, hGH (human growth hormone), cytokines (e.g., interleukin, interferon, colony-stimulating factor, and tumor necrosis factor), testosterone, methyltestosterone, progesterone, estradiol, derivatives thereof, and combinations thereof.

The above peptides, proteins, and hormones include not only naturally occurring substances but pharmacologically active derivatives thereof and analogues thereof. For example, calcitonin includes not only naturally occurring products such as salmon calcitonin, human calcitonin, porcine calcitonin, eel calcitonin, and fowl calcitonin, but also includes analogues, such as [Asu1,7]-eel calcitonin (Elcatonin). Further, insulin includes human insulin, porcine insulin, bovine insulin, as well as their analogues, such as recombinant insulin.

Suitable anti-inflammatory agents include, without limitation, drugs that are effective against diseases and disorders of the gastrointestinal tract, such as Crohn's disease, ulcerative colitis, irritable colitis, and colon cancer. Examples of such drugs include salazosulfapyridine, 5-aminosalicylic acid, cortisone acetate, triamcinolone, dexamethasone, budesonide, tegafur, fluorouracil, derivatives thereof, and combinations thereof. Steroidal and non-steroidal anti-inflammatory agents are also within the scope of the present invention.

Other drugs suitable for use in the present invention include antitussive expectorants such as theophylline; vasodilators such as nicardipine hydrochloride and nifedipine; coronary vasodilators such as isosorbide nitrite; and antipyretic analgesics such as acetaminophen, indomethacin, hydrocortisone, ibuprofen, salazopyrin, pharmaceutically acceptable salts thereof, derivatives thereof, and combinations thereof.

Suitable histamine $H_2$-receptor antagonists include, without limitation, famotidine, cimetidine, ranitidine, roxatidine acetate, pharmaceutically acceptable salts thereof, derivatives thereof, and combinations thereof.

Suitable antibiotics include, without limitation, tetracycline, oxytetracycline, metacycline, doxycycline, minocycline, erythromycin, lincomycin, penicillin G, clindamycin, kanamycin, chloramphenicol, fradiomycin, streptomycin, norfloxacin, ciprofloxacin, ofloxacin, grepafloxacin, levofloxacin, sparfloxacin, ampicillin, carbenicillin, methicillin, cephalosporins, vancomycin, bacitracin, gentamycin, fusidic acid, ciprofloxin and other quinolones, sulfonamides, trimethoprim, dapsone, isoniazid, teicoplanin, avoparcin, synercid, virginiamycin, piperacillin, ticarcillin, cefepime, cefpirome, rifampicin, pyrazinamide, enrofloxacin, amikacin, netilmycin, imipenem, meropenem, inezolidcefuroxime, ceftriaxone, cefadroxil, cefazoline, ceftazidime, cefotaxime, roxithromycin, cefaclor, cefalexin, cefoxitin, amoxicillin, co-amoxiclav, mupirocin, cloxacillin, co-trimoxazole, pharmaceutically acceptable salts thereof, derivatives thereof, and combinations thereof.

Suitable antiepileptic agents include, without limitation, ethosuximide, sodium valproate, acetazolamide, meprobamate, and the like, as well as antiparkinsonism drugs such as chlorzoxazone, levodopa, pharmaceutically acceptable salts thereof, derivatives thereof, and combinations thereof.

Suitable antigout agents include, without limitation, allopurinol, colchicines, benzbromarone, pharmaceutically acceptable salts thereof, derivatives thereof, and combinations thereof.

Suitable antitumor agents include, without limitation, 5-fluorouracil, uracil, cytarabine, floxuridine, busulfan, actinomycin, bleomycin, mitomycin, pharmaceutically acceptable salts thereof, derivatives thereof, and combinations thereof.

Suitable antidiabetic agents include, without limitation, glibenclamide, epalrestat, pharmaceutically acceptable salts thereof, derivatives thereof, and combinations thereof.

Suitable antipsychotic agents include, without limitation, emonaprode, diazepam, nitrazepam, flunitrazepam, lorazepam, prazepam, fluidiazepam, clonazepam, chlorpromazine hydrochloride, reserpine, clofluperol, trifluperidol, haloperidol, moperone, bromperidom, etizolam, pharmaceutically acceptable salts thereof, derivatives thereof, and combinations thereof.

Suitable prostatomegaly agents include, without limitation, chlormadinone acetate, pharmaceutically acceptable salts thereof, derivatives thereof, and combinations thereof.

Suitable antiasthma agents include, without limitation, azelastine, procaterol, terrenadine, pharmaceutically acceptable salts thereof, derivatives thereof, and combinations thereof.

In order to make these drugs more easily absorbable in the colon, one or more pharmaceutically acceptable additives can be added to the drug. Suitable additives include, without limitation, surface active agents such as sucrose fatty acid esters (e.g., Sugar Ester L1695, produced by Mitsubishi Chemical Foods Co., Ltd.), sodium laurylsulfate, polyoxyethylene hydrogenated castor oil (e.g., HCO-60), and polyoxyethylene sorbitan higher fatty acid esters (e.g., Tween 80); cholic acids and salts thereof such as sodium glycocholate and chenodeoxycholic acid; organic acids and salts thereof such as citric acid, tartaric acid, benzoic acid, and capric acid; dissolution aids such as β-cyclodextrin; pH adjusters such as sodium citrate, meglumine, and MgO; trypsin inhibitors such as camostat mesilate; enzyme inhibitors such as aprotinin; anti-inflammatory agents such as salicylic acid, aspirin, sodium dichlofenac; aromas such as peppermint oil; and antibiotics such as bacitracin and amphotericin B.

Regardless of whether a drug is acidic or basic, the pH of the system can be adjusted at the time of drug dissolution, e.g., by incorporating a buffering agent such as an organic acid or a basic substance into one or more drug-containing layers. The organic acids include citric acid and tartaric acid, and the basic substances include solid bases (e.g., MgO), basic amino-sugars (e.g., meglumine), and basic amino acids (e.g., lysine and arginine). Such buffering agents can be mixed with the drug and saccharide to form the drug core, with the drug to form the drug layer, with the drug to form the outer drug coat, or with the enteric coating polymer and the drug to form the enteric coat.

For a drug that has low solubility at pH 6 or lower, a dissolution aid can be added. Any dissolution aid is suitable for use, as long as it is pharmaceutically acceptable. Examples include, without limitation, nonionic surface active agents such as sucrose fatty acid esters, glycerol fatty acid esters, sorbitan fatty acid esters (e.g., sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g., chenodeoxycholic acid, cholic acid, deoxycholic acid, dehydrocholic acid and salts thereof, and glycine or taurine conjugate thereof); ionic surface active agents such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents such as betaines and aminocarboxylic acid salts.

B. Saccharides

The saccharides used in the present invention, which are degraded by enterobacteria in the lower gastrointestinal tract to generate an organic acid, are not limited by whether they are monosaccharides or polysaccharides as long as they are rapidly degraded by enterobacteria to produce the organic acid. Disaccharides or polysaccharides which are not degraded by digestive enzymes in the gastrointestinal tract or not absorbed directly from the gastrointestinal tract are preferred. It is preferable for the saccharide to be rapidly dissolved and degraded to produce the organic acid. Accordingly, those saccharides having high water solubility are preferred. Specifically, the amount of water which is required to dissolve a 1 g portion of saccharide is preferably less than about 5 ml; that is, saccharides having a water solubility of higher than about 20% weight/volume (w/v) are preferred. Examples of such saccharides include, without limitation, lactulose, raffinose, cellobiose, stachyose, fructooligosaccharides (i.e., synthetic disaccharides which show a high rate of degradation by enterobacteria), combinations thereof, and derivatives thereof (e.g., sugar alcohols such as mannitol, sorbitol, xylitol, and maltitol). The fructooligosaccharides preferably include lactosucrose, such as Nyuka Oligo LS-55p (Hayashibara Syoji K. K.). In addition to saccharides, other carbohydrates are also suitable for use in the systems of the present invention.

Saccharides which are degraded by digestive enzymes or directly absorbed from the gastrointestinal tract can be employed in a similar manner. Such saccharides are prevented from degradation in the stomach by the presence of an enteric coat and are prevented from degradation in the small intestine by the presence of an organic acid-soluble polymer coat. Examples of saccharides of this type include, without limitation, sucrose, glucose, xylose, fructose, maltose, galactose, and combinations thereof.

Any amount of saccharide is suitable for degradation by enterobacteria to produce an organic acid. In particular, the saccharide is present in an amount of from about 1% to about 99.9% w/w, preferably from about 5% to about 99.9% w/w, and more preferably from about 10% to about 90% w/w.

C. Organic Acid-Soluble Polymers

Any organic acid-soluble polymer material is suitable for use in the systems of the present invention as long as it is pharmaceutically acceptable. Polymers which dissolve at a pH lower than about 6 are preferable, and those that dissolve at about pH 5.5 or lower are more preferable. Specific examples of such polymers include, without limitation, a dimethylaminoethyl methacrylate-methyl methacrylate copolymer such as a dimethylaminoethyl methacrylate-methyl methacrylate-butyl methacrylate copolymer (e.g., Eudragit E), polyvinyl acetal diethylaminoacetate (e.g., AEA; Sankyo Co., Ltd.), chitosan, and combinations thereof. Preferably, the organic acid-soluble polymer is a dimethylaminoethyl methacrylate-methyl methacrylate-butyl methacrylate copolymer (e.g., Eudragit E). The organic acid-soluble polymer is present in an amount of from about 1% to about 50% w/w, preferably from about 2.5% to about 40% w/w.

D. Water-Permeable, Release-Controlling Polymers

The water permeable, release-controlling polymer material serves as a barrier layer between the organic acid-soluble polymer coat and the enteric coat to prevent any interaction between these polymer coats. The polymer can also serve as a protecting layer for controlling the release of the organic acid-generating saccharide from the drug core or for preventing diffusion of the drug(s) therein. Suitable examples of water permeable, release-controlling polymers include, without limitation, a copolymer of ethyl acrylate, methyl methacrylate, and trimethylammonioethyl methacrylate chloride (e.g., Eudragit RS; Röhm GmbH), ethyl cellulose (e.g., Ethocel; Dow Chemical Co., Ltd.), hydroxypropyl-methylcellulose (HPMC) (e.g., TC-5; Shin-Etsu Chemical Co., Ltd.), hydroxypropylcellulose (e.g., HPC; Nippon Soda Co., Ltd.), polyethylene oxide, polyvinylpyrrolidone, and combinations thereof. Preferably, the water permeable, release-controlling polymer is hydroxypropylmethylcellulose. The polymer can further comprise a plasticizer such as triacetin, Macrogol 400, triethyl citrate, Tween 80, castor oil, etc. The water permeable, release-controlling polymer is present in an amount of from about 1% to about 50% w/w, preferably from about 1% to about 20% w/w, and more preferably from about 1% to about 10% w/w.

E. Enteric Coats

The enteric coating polymer material, i.e., the polymer which does not dissolve in the stomach but in the small intestine, can be any pharmaceutically-acceptable polymer material. In particular, polymer materials which dissolve at a pH of about 6 or higher are preferred. Examples of suitable enteric coating polymers include, without limitation, a methyl methacrylate-methacrylic acid (1:1) copolymer (e.g., Eudragit L; Röhm & Haas Co.), a methyl methacrylate-methacrylic acid (2:1) copolymer (e.g., Eudragit S; Röhm & Haas Co.), an ethyl acrylate-methacrylic acid (1:1) copolymer (e.g., Eudragit LD-55; Röhm & Haas Co.), hydroxypropylmethylcellulose phthalate (JPXII), cellulose acetate phthalate (JPXII), shellac (JPXII), and combinations thereof. Preferably, the enteric coating polymer is a methyl methacrylate-methacrylic acid (1:1) copolymer (e.g., Eudragit L). The polymer can further comprise a plasticizer such as triacetin, Macrogol 400, triethyl citrate, Tween 80, castor oil, etc., as well as minerals such as magnesium silicate hydroxide (i.e., talc). The enteric coating polymer is present in an amount of from about 1% to about 50% w/w, preferably from about 1% to about 20% w/w, more preferably from about 1% to about 10% w/w. In a preferred embodiment, the enteric coat comprises an enteric coating polymer (e.g., Eudragit L100), triethyl citrate, magnesium silicate hydroxide (i.e., talc), and optionally, a drug and a buffering agent.

In addition to the elements described above, the oral drug delivery systems of the present invention can also comprise pharmaceutically acceptable excipients such as carriers, binders, stabilizers, bulking agents, preserving agents (e.g., methyl-, ethyl-, and propyl-hydroxy-benzoates, butylated hydroxytoluene, butylated hydroxyanisole), sweetening agents, flavoring agents, coloring agents, lubricating agents, wetting agents, emulsifying agents, solubilizing agents, suspending agents, and disintegrating agents (e.g., crospovidone, croscarmellose sodium). The system can be provided in any dosage form suitable for oral administration such as a tablet, a capsule, a pellet, a granule, fine granules, a lozenge, and a powder. Preferably, the system is administered in the form of a tablet or capsule.

V. Enterobacteria

Bacteria which live within the body are abundant in the oral cavity, rare in the stomach due to the acidity, and also scarce in the upper part of the small intestine. The level of enterobacteria increases drastically in the order of the ileum, the cecum, and the colon. It has been reported that saccharides which remain undigested are degraded by enterobacteria residing in the part of the gastrointestinal tract from the cecum to the ascending colon, making that part weakly acidic (e.g., pH of about 5) (Davis, *Novel Drug Delivery and its Therapeutic Application*, p. 89-101, Eds. L. F. Prescott, W. S. Nimmo; John Willey & Sons, New York).

A remarkable feature observed is an increase in anaerobic bacteria from the ileum to the colon. In humans, Bacteroidaceae, *Bifidobacterium* sp., *Eubacterium* sp., *Clostridium* sp., and *Peptococcaceae* constitute the main microbial flora, but Enterobacteriaceae sp., *Streptococcus* sp., *Lactobacillus* sp., and *Veillonella* sp. are also present. The intestinal microbial flora does not change within a healthy individual but varies among individuals or with stress, diet, or disease. The variation is limited to specific enterobacteria and is not so large that all the microbial flora contributing to degradation of saccharides cannot be detected. When the enterobacteria absorb and metabolize saccharides, various organic acids are generated. The organic acids generated include acetic acid, propionic acid, and butyric acid, and vary according to the saccharide substrate. These organic acids are absorbed from the intestinal tract and become an energy source.

The enterobacteria *Bifidobacterium*, *Lactobacillus*, and *Streptococcus*, present in the lower gastrointestinal tract (i.e., the colon), are mainly responsible for degrading saccharides such as lactulose (i.e., a synthetic disaccharide) to produce an organic acid such as lactic acid, acetic acid, etc. Diabetics show a slight reduction in *Bifidobacterium* and *Streptococcus*, but this does not seem to have large influence on the degradation of lactulose as no change was observed in *Lactobacillus*. Raffinose, cellobiose, stachyose, maltose, and fructooligosaccharides are rapidly degraded by the main microbial flora in the colon similarly to lactulose, although they are degraded by slightly different enterobacteria. Accordingly, slight variations in the microbial flora of the colon will not affect the degradation of these saccharides.

Without being bound to any particular theory, the organic acid which is generated by the action of enterobacteria serves to decrease the pH of the system, thereby dissolving the organic acid-soluble polymer coat on the drug core as well as contributing to the enhancement of drug absorption in the colon.

VI. Methods of Manufacturing

Figure 6:
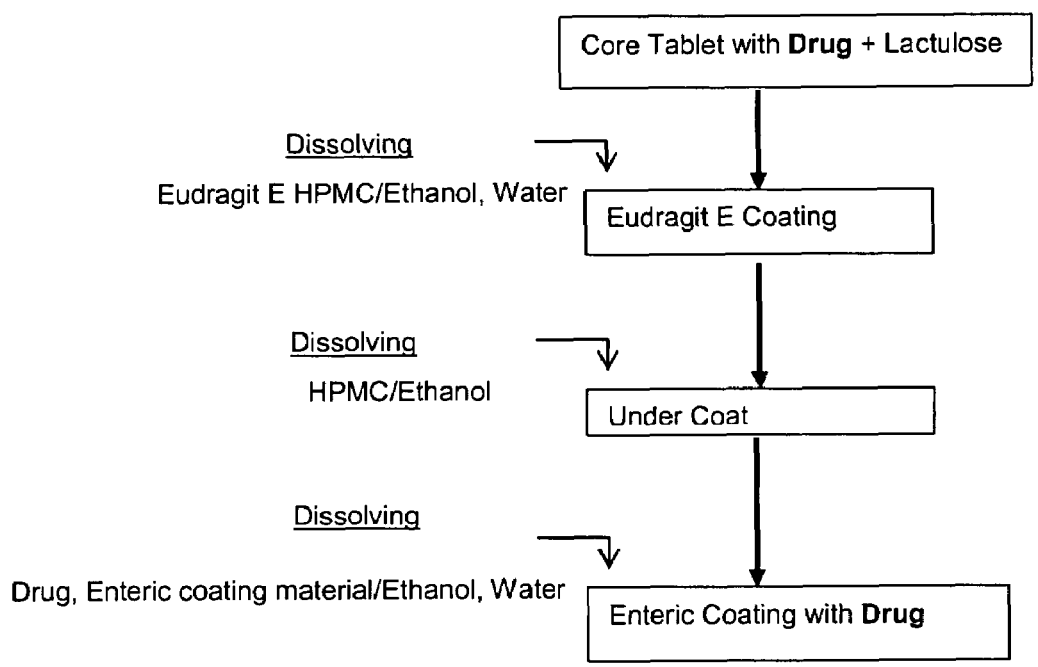
FIG. 6 shows a manufacturing flowchart for producing the multiple release tablet of FIG. 1.

FIG. 6 shows a manufacturing flowchart for producing the spray-coated tablet of FIG. 1. In one embodiment, a first drug is mixed with a saccharide (e.g., lactulose), and optionally, a buffering agent, to produce a homogeneous mixture that forms the drug core of the tablet. An organic acid-soluble polymer (e.g., Eudragit E) coat is then sprayed onto the drug core. The organic acid-soluble polymer coat is prepared, e.g., by dissolving Eudragit E and HPMC in ethanol and water. In an alternative embodiment, the drug core of the tablet is formed by spraying a saccharide coat onto the first drug, followed by the spraying of an organic acid-soluble polymer coat. A water-permeable, release-controlling polymer (e.g., HPMC) can optionally be included as a coat for the drug core. In both embodiments, an under coat comprising a water-permeable, release-controlling polymer (e.g., HPMC) is sprayed onto the organic acid-soluble polymer coat. The under coat is prepared, e.g., by dissolving HPMC in ethanol. Finally, an enteric coat, prepared by dissolving a mixture of an enteric coating polymer material and a second drug in ethanol and water, is sprayed onto the tablet under coat to produce the multiple drug release tablet as shown in FIG. 1.

Figure 7:
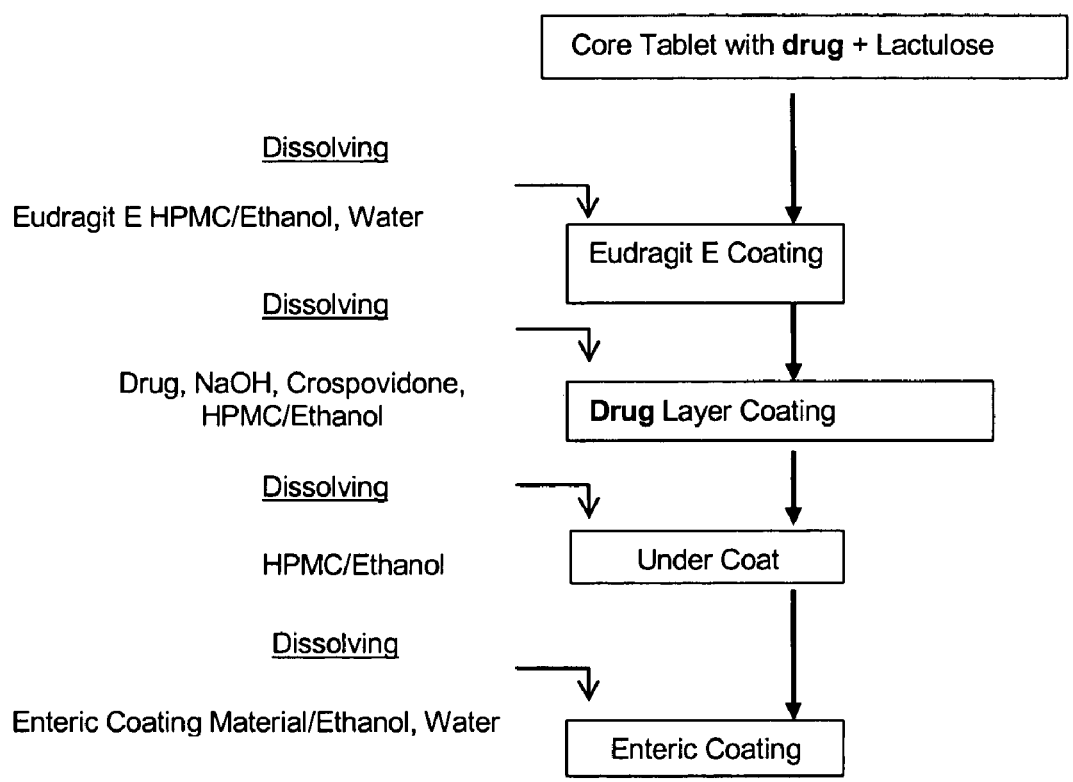
FIG. 7 shows a manufacturing flowchart for producing the multiple release tablet of FIG. 3.

FIG. 7 shows a manufacturing flowchart for producing the spray-coated tablet of FIG. 3. In one embodiment, a first drug is mixed with a saccharide (e.g., lactulose), and optionally, a buffering agent, to produce a homogeneous mixture that forms the drug core of the tablet. An organic acid-soluble polymer (e.g., Eudragit E) coat is then sprayed onto the drug core. The organic acid-soluble polymer coat is prepared, e.g., by dissolving Eudragit E and HPMC in ethanol and water. In an alternative embodiment, the drug core of the tablet is formed by spraying a saccharide coat onto the first drug, followed by the spraying of an organic acid-soluble polymer coat. A water-permeable, release-controlling polymer (e.g., HPMC) can optionally be included as a coat for the drug core. In both embodiments, a drug layer comprising a second drug is sprayed onto the organic acid-soluble polymer coat. The drug layer is prepared, e.g., by dissolving the second drug with NaOH, crospovidone, and HPMC in ethanol. The drug layer is then sprayed with an under coat comprising a water-permeable, release-controlling polymer (e.g., HPMC). The under coat is prepared, e.g., by dissolving HPMC in ethanol. Finally, an enteric coat, prepared by dissolving an enteric coating polymer material in ethanol and water, is sprayed onto the tablet under coat to produce the multiple drug release tablet as shown in FIG. 3.

Figure 8:
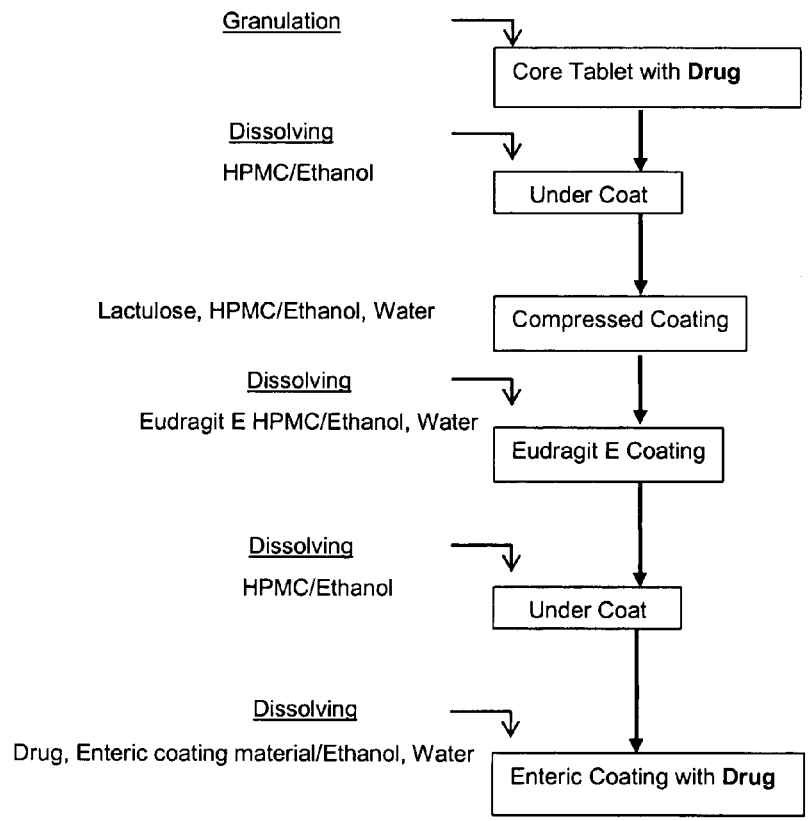
FIG. 8 shows a manufacturing flowchart for producing the multiple release tablet of FIG. 4.

FIG. 8 shows a manufacturing flowchart for producing the compressed-coated tablet of FIG. 4. In one embodiment, a first drug is optionally mixed with a buffering agent to produce a homogeneous mixture. A saccharide (e.g., lactulose) layer is then compressed onto the first drug to form the drug core of the tablet. The saccharide layer is prepared, e.g., by dissolving lactulose and HPMC in ethanol and water. A water-permeable, release-controlling polymer (e.g., HPMC) can optionally be included in the drug core as an under coat in between the first drug and the saccharide. An organic acid-soluble polymer (e.g., Eudragit E) coat is then sprayed onto the drug core. The organic acid-soluble polymer coat is prepared, e.g., by dissolving Eudragit E and HPMC in ethanol and water. An under coat comprising a water-permeable, release-controlling polymer (e.g., HPMC) is then sprayed onto the organic acid-soluble polymer coat. The under coat is prepared, e.g., by dissolving HPMC in ethanol. Finally, an enteric coat, prepared by dissolving a mixture of an enteric coating polymer material and a second drug in ethanol and water, is sprayed onto the tablet under coat to produce the multiple drug release tablet as shown in FIG. 4.

Figure 9:
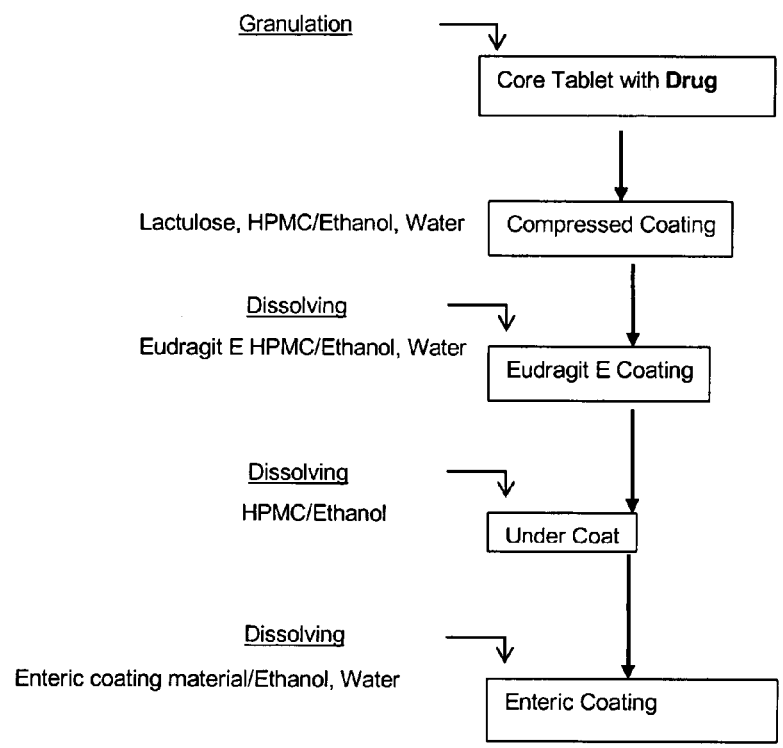
FIG. 9 shows a manufacturing flowchart for producing the colon-targeted tablet in the capsule of FIG. 5.

FIG. 9 shows a manufacturing flowchart for producing the colon-targeted tablet (B) in the capsule of FIG. 5. In one embodiment, a first drug is optionally mixed with a buffering agent to produce a homogeneous mixture. A saccharide (e.g., lactulose) layer is then compressed onto the first drug to form the drug core of the tablet. The saccharide layer is prepared, e.g., by dissolving lactulose and HPMC in ethanol and water. A water-permeable, release-controlling polymer (e.g., HPMC) can optionally be included in the drug core as an under coat in between the first drug and the saccharide. An organic acid-soluble polymer (e.g., Eudragit E) coat is then sprayed onto the drug core. The organic acid-soluble polymer coat is prepared, e.g., by dissolving Eudragit E and HPMC in ethanol and water. An under coat comprising a water-permeable, release-controlling polymer (e.g., HPMC) is sprayed onto the organic acid-soluble polymer coat. The under coat is prepared, e.g., by dissolving HPMC in ethanol. Finally, an enteric coat, prepared by dissolving an enteric coating polymer material in ethanol and water, is sprayed onto the tablet under coat to produce the multiple drug release tablet as shown in FIG. 5.

EXAMPLES

The following examples are offered to illustrate, but not to limit, the claimed invention.

Example 1

Famotidine Multiple Release Tablet

A dual release tablet for delivering two 10 mg pulses of the histamine $H_2$-receptor antagonist famotidine (total 20 mg per day) can be formulated using a spray-coated tablet manufacturing process. The tabletting pressure is about 350 kg/punch. The initial release of drug is provided by the enteric coat. The formulation contains:

| Drug core: | |
|---|---|
| Famotidine | 10 mg |
| Lactulose | 100 mg |
| Total: | 110 mg |

Famotidine ($t_{1/2}$=3 hrs.), lactulose, and optionally other additives are mixed to prepare the drug core. The drug core is first coated with about 10% w/w of Eudragit E100 (e.g., 9.5% w/w of Eudragit E100 in a 71:29 mixture of ethyl alcohol: water), based on the gained weight of the drug core, and then coated with a layer of from about 1% to about 10% w/w of HPMC (e.g., 5% HPMC 2910 in an aqueous solution) by means of a Hi-coater. The drug core tablet is subsequently coated with from about 5% to about 10% w/w of Eudragit L100 containing 10 mg of famotidine and optionally a buffering agent and other additives (e.g., 6% Eudragit L100, 10 mg of famotidine, 1% triethyl citrate, and 3% talc in a 71:29 mixture of ethyl alcohol:water) to obtain the multiple-pulsated drug release tablet of the present invention. The tablet has a diameter of about 6 mm.

Example 2

Minocycline Multiple Release Tablet

A dual release tablet for delivering two 50 mg pulses of the antibiotic minocycline (total 100 mg per day) can be formulated using a spray-coated tablet manufacturing process. The tabletting pressure is about 350 kg/punch. The initial release of drug is provided by a separate drug layer. The formulation contains:

| Drug core: | |
|---|---|
| Minocycline hydrochloride | 50 mg |
| Lactulose | 50 mg |
| Total: | 100 mg |

Minocycline hydrochloride ($t_{1/2}$=9.5 hrs.), lactulose, and optionally other additives are mixed to prepare the drug core. The drug core is first coated with about 10% w/w of Eudragit E100 (e.g., 9.5% w/w of Eudragit E100 in a 71:29 mixture of ethyl alcohol:water) and then coated with HPMC containing 50 mg of minocycline hydrochloride. The drug core tablet is subsequently coated with a layer of from about 1% to about 10% w/w of HPMC (e.g., 5% HPMC 2910 in an aqueous solution) by means of a Hi-coater. Finally, the tablet is coated with from about 5% to about 10% w/w of Eudragit L100 and optionally additives (e.g., 6% Eudragit L100, 1% triethyl citrate, and 3% talc in a 71:29 mixture of ethyl alcohol:water) to obtain the multiple-pulsated drug release tablet of the present invention. The tablet has a diameter of about 6 mm.

Example 3

Allopurinol Multiple Release Tablet

A dual release tablet for delivering two 100 mg pulses of the antigout agent allopurinol (total 200 mg per day) can be formulated using a spray-coated tablet manufacturing process. The tabletting pressure is about 350 kg/punch. The initial release of drug is provided by a separate drug layer. The formulation contains:

| Drug core: | |
|---|---|
| Allopurinol | 100 mg |
| Lactulose | 100 mg |
| Meglumine | 20 mg |
| Total: | 220 mg |

Allopurinol ($t_{1/2}$=1.6 hrs.), lactulose, meglumine (for neutralization), and optionally other additives are mixed to prepare the drug core. The drug core is first coated with about 10% w/w of Eudragit E100 (e.g., 9.5% w/w of Eudragit E100 in a 71:29 mixture of ethyl alcohol:water) and then coated with HPMC containing 100 mg allopurinol. The drug core tablet is subsequently coated with a layer of from about 1% to about 10% w/w of HPMC (e.g., 5% HPMC 2910 in an aqueous solution) by means of a Hi-coater. Finally, the tablet is coated with from about 5% to about 10% w/w of Eudragit L100 and optionally additives (e.g., 6% Eudragit L100, 1% triethyl citrate, and 3% talc in a 71:29 mixture of ethyl alcohol:water) to obtain the multiple-pulsated drug release tablet of the present invention. The tablet has a diameter of from about 7 to about 9 mm.

Example 4

Omeprazole Multiple Release Tablet

A dual release tablet for delivering two 10 mg pulses of the proton pump inhibitor omeprazole (total 20 mg per day) can be formulated using a compressed-coated tablet manufacturing process. The tabletting pressure is about 350 kg/punch. The initial release of drug is provided by the enteric coat. The formulation contains:

| Drug core: | |
|---|---|
| Omeprazole | 10 mg |
| Lactulose | 100 mg |
| MgO | 10 mg |
| Total: | 120 mg |

Omeprazole ($t_{1/2}$=1.8 hrs.), lactulose, MgO, and optionally other additives are mixed to prepare the drug core. First, the drug core is coated with from about 1-2% w/w of HPMC by means of a Hi-coater. The lactulose layer is then placed onto the drug core tablet using a compressed coating machine. The tablet is subsequently coated with about 10% w/w of Eudragit E100 (e.g., 9.5% w/w of Eudragit E100 in a 71:29 mixture of ethyl alcohol:water) and then coated with a layer of from about 1% to about 10% w/w of HPMC (e.g., 5% HPMC 2910 in an aqueous solution) by means of a Hi-coater. Finally, the tablet is coated with from about 5% to about 10% w/w of Eudragit L100 containing 10 mg of omeprazole and optionally a buffering agent and other additives (e.g., 6% Eudragit L100, 10 mg of omeprazole, 1% triethyl citrate, and 3% talc in a 71:29 mixture of ethyl alcohol:water) to obtain the multiple-pulsated drug release tablet of the present invention. The tablet has a diameter of about 6 mm.

In certain instances, MgO (magnesium oxide) is used as a buffering agent in formulations with drugs that are unstable under acidic conditions to adjust the pH such that an alkaline environment is maintained inside the tablet. As described above, regardless of whether a drug is acidic or basic, the pH of the system can be adjusted at the time of drug dissolution, e.g., by incorporating a buffering agent such as an organic acid or a basic substance into one or more drug-containing layers. The organic acids include citric acid and tartaric acid, and the basic substances include solid bases (e.g., MgO), basic amino-sugars (e.g., meglumine), and basic amino acids (e.g., lysine and arginine).

Example 5

Omeprazole Multiple Release Capsule

A dual release capsule for delivering two 10 mg pulses of the proton pump inhibitor omeprazole (total 20 mg per day) can be formulated using a manufacturing process that produces a capsule containing both a spray-coated enteric coated tablet and a compressed-coated colon-targeted tablet. The initial release of drug is provided by the enteric coated tablet. Each drug core contains 10 mg of the proton pump inhibitor omeprazole, for the release of a total of 20 mg per day. The manufacturing process for the colon-targeted compressed-coated tablet is similar to that described in Example 4. However, the enteric coat may or may not contain drug. The enteric coated tablet is prepared by spray-coating a layer of HPMC onto the drug core followed by an enteric coat layer. Both tablets are then encapsulated to produce a capsule suitable for oral administration.

Figure 10:
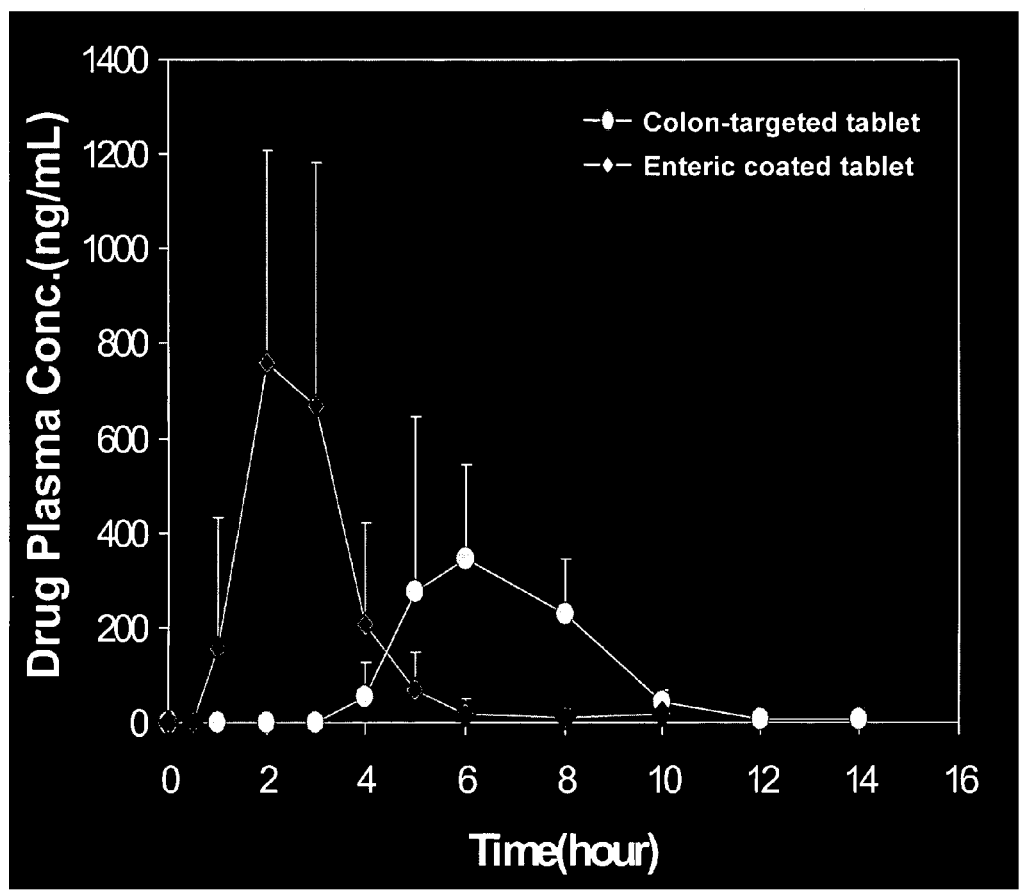
FIG. 10 shows a representative pharmacokinetic profile for the capsule of the present invention which contains an enteric coated tablet and a colon-targeted tablet.

A representative pharmacokinetic profile for a capsule within the scope of the present invention using acetaminophen as a model drug for dog studies is shown in FIG. 10. The initial release of drug from the enteric coated tablet provides a steady concentration of drug in the plasma from about 0.5 hours to about 6 hours following administration. The subsequent release of drug from the colon-targeted tablet sustains the concentration of drug in the plasma for up to about 12 hours following administration. However, one skilled in the art will recognize that the concentration of drug in the plasma can be sustained for about 24 hours or more for drugs with longer half-lives ($t_{1/2}$).

Example 6

Proton Pump Inhibitor Multiple Release System

The proton pump inhibitor in the formulations of Examples of 4 and 5 can be replaced with other proton pump inhibitors such as lansoprazole, pantoprazole, esomeprazole rabeprazole, and combinations thereof.

Example 7

Comparison of Drug Release and Pharmacokinetic Profiles

This example illustrates a comparison of the in vivo drug release and pharmacokinetic profiles of a standard colon drug delivery system versus the multiple drug release system of the present invention.

Figure 11:
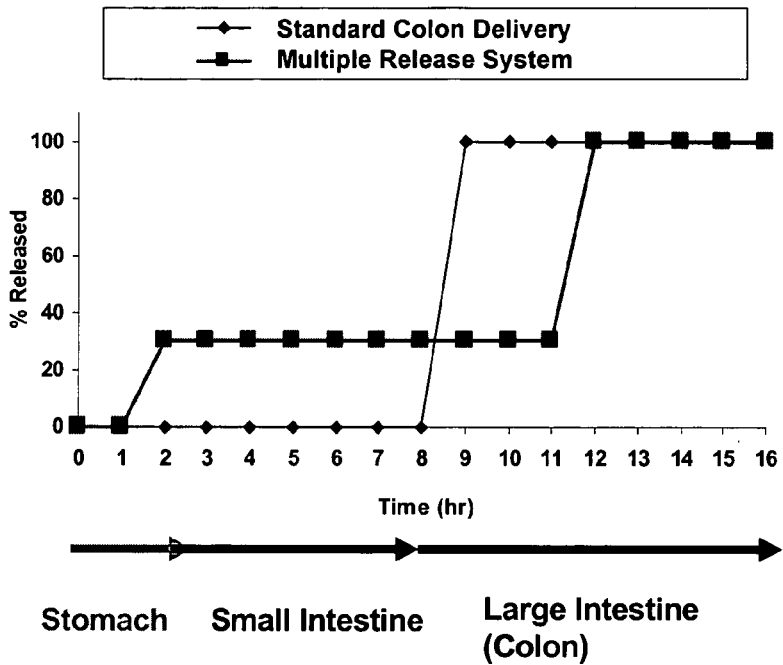
FIG. 11 shows a comparison of the in vivo drug release profile (FIG. 11A) and the pharmacokinetic profile (FIG. 11B) of a standard colon drug delivery system versus the multiple drug release system of the present invention.
Figure 11:
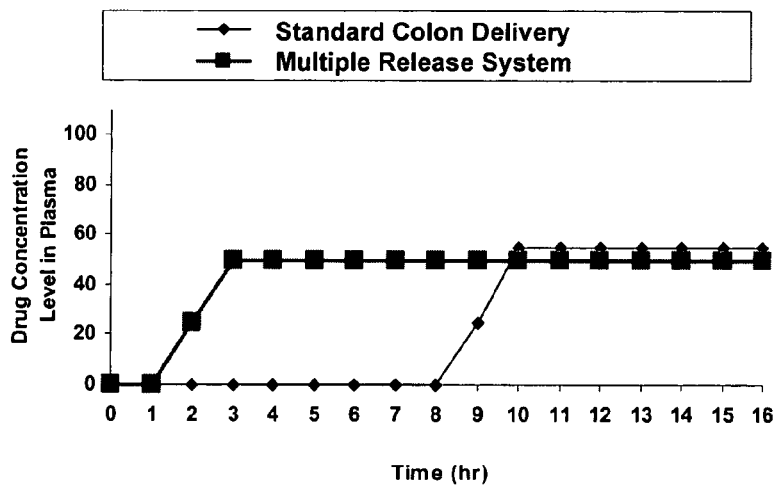

As shown in FIG. 11A, a standard colon drug delivery system only begins to release drug in the gastrointestinal tract about 8 hours following administration. By contrast, the multiple drug release system of the present invention provides an initial release of drug in the small intestine starting at about 1 hour following oral administration and a subsequent release of drug in the colon starting at about 11 following oral administration. As a result, the release of drug is sustained for a longer period of time (e.g., about 24 hours).

FIG. 11B shows the level of drug in the plasma at certain time points following administration of either a standard colon delivery system or the multiple drug release system of the present invention. Upon administration of a standard colon delivery system, the presence of drug in the plasma is only detected after about 8 hours. By contrast, upon administration of the multiple drug release system of the present invention, the concentration of drug in the plasma begins to increase after about 1 hour, reaches a steady level at about 3 hours, and maintains a constant level of drug in the plasma for about 24 hours or more. As a result, the concentration of drug in the plasma is sustained for a longer period of time (e.g., about 24 hours).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An oral multiple drug release composition, said composition comprising:
(a) a drug core comprising a first drug and a saccharide, wherein said first drug is coated by said saccharide;
(b) a water-permeable, release-controlling polymer as a layer in between said first drug and said saccharide;
(c) an organic acid-soluble polymer, wherein said drug core is coated by said organic acid-soluble polymer;
(d) a water-permeable, release-controlling polymer, wherein said organic acid-soluble polymer is coated by said water-permeable, release-controlling polymer; and
(e) an enteric coat comprising a mixture of an enteric coating polymer and a second drug, wherein said water-permeable, release-controlling polymer is coated by said enteric coat,
wherein said composition releases said second drug in the small intestine and said first drug in the colon.

2. The composition of claim 1, wherein said drug core comprises a mixture of said first drug and said saccharide.

3. The composition of claim 1, wherein said first drug and said second drug are the same drug.

4. The composition of claim 1, wherein said first drug and said second drug are different drugs.

5. The composition of claim 1, wherein said first drug is a combination of at least two drugs.

6. The composition of claim 1, wherein said first drug and said second drug are independently selected from the group consisting of a proton pump inhibitor, a peptide, a protein, a hormone, an anti-inflammatory agent, an antitussive expectorant, a vasodilator, an analgesic, a histamine $H_2$-receptor antagonist, an antibiotic, an antiepileptic agent, an antigout agent, an antitumor agent, an antidiabetic agent, an antipsychotic agent, a prostatomegaly agent, an antiasthma agent, a drug with a short pharmacokinetic half-life, pharmaceutically acceptable salts thereof, derivatives thereof, and combinations thereof.

7. The composition of claim 6, wherein said proton pump inhibitor is selected from the group consisting of omeprazole, esomeprazole, lansoprazole, rabeprazole, pantoprazole, pharmaceutically acceptable salts thereof, derivatives thereof, and combinations thereof.

8. The composition of claim 1, wherein said drug core further comprises a buffering agent.

9. The composition of claim 1, wherein said enteric coat further comprises a buffering agent.

10. The composition of claim 1, wherein said saccharide is selected from the group consisting of lactulose, raffinose, cellobiose, stachyose, fructoligosaccharide, sucrose, glucose, xylose, fructose, mannitol, maltose, galactose, and combinations thereof.

11. The composition of claim 10, wherein said saccharide is lactulose.

12. The composition of claim 10, wherein said saccharide is present in an amount of from about 10% to about 90% w/w.

13. The composition of claim 1, wherein said organic acid-soluble polymer is selected from the group consisting of a dimethylaminoethyl methacrylate-methyl methacrylate copolymer, a polyvinyl acetal diethylaminoacetate, chitosan, and combinations thereof.

14. The composition of claim 13, wherein said dimethylaminoethyl methacrylate-methyl methacrylate copolymer is a dimethylamino ethyl methacrylate-methyl methacrylate-butyl methacrylate copolymer.

15. The composition of claim 13, wherein said organic acid-soluble polymer is present in an amount of from about 2.5% to about 40.0% w/w.

16. The composition of claim 13, wherein said organic acid-soluble polymer dissolves at a pH lower than about 6.

17. The composition of claim 1, wherein said water-permeable, release-controlling polymer is selected from the group consisting of a copolymer of ethyl acrylate, methyl methyacrylate, and trimethylammonioethyl methacrylate chloride, ethyl cellulose, hydroxypropylmethylcellulose (HPMC), hydroxypropylcellulose, polyethylene oxide, polyvinylpyrrolidone, and combinations thereof.

18. The composition of claim 17, wherein said water-permeable, release-controlling polymer is HPMC.

19. The composition of claim 1, wherein said enteric coating polymer is selected from the group consisting of a methyl methacrylate-methylacrylate acid (1:1) copolymer, a methyl methacrylate-methacrylate acid (2:1) copolymer, an ethyl acrylate-methacrylic acid (1:1) copolymer, hydroxypropylmethylcellulose phthalate, cellulose acetate phthalate, shellac, and combinations thereof.

20. The composition of claim 1, further comprising an outer drug coat having a third drug, wherein said enteric coat is coated by said outer drug coat and said composition releases said third drug in the stomach.

21. The composition of claim 1, wherein said composition is in the form of a tablet or granule.

22. The composition of claim 1, wherein said drug core comprises a mixture of a first proton pump inhibitor and lactulose, said organic acid-soluble polymer is a dimethylamino ethyl methacrylate-methyl methacrylate-butyl methacrylate copolymer, said water-permeable, release-controlling polymer is HPMC, and said enteric coat comprises a mixture of an enteric coating polymer and a second proton pump inhibitor.

23. An oral multiple drug release composition, said composition comprising:
(a) a drug core comprising a first drug;
(b) a saccharide, wherein said drug core is coated by said saccharide;
(c) a water-permeable, release-controlling polymer as a layer in between said first drug and said saccharide, admixed with said first drug, or a combination thereof;
(d) an organic acid-soluble polymer, wherein said saccharide is coated by said organic acid-soluble polymer;
(e) a water-permeable, release-controlling polymer, wherein said organic acid-soluble polymer is coated by said water-permeable, release-controlling polymer; and
(f) an enteric coat comprising a mixture of an enteric coating polymer and a second drug, wherein said water-permeable, release-controlling polymer is coated by said enteric coat,
wherein said composition releases said second drug in the small intestine and said first drug in the colon.

24. The composition of claim 23, wherein said first drug and said second drug are the same drug.

25. The composition of claim 23, wherein said first drug and said second drug are different drugs.

26. The composition of claim 23, wherein said first drug is a combination of at least two drugs.

27. The composition of claim 23, wherein said first drug and said second drug are independently selected from the group consisting of a proton pump inhibitor, a peptide, a protein, a hormone, an anti-inflammatory agent, an antitussive expectorant, a vasodilator, an analgesic, a histamine $H_2$-receptor antagonist, an antibiotic, an antiepileptic agent, an antigout agent, an antitumor agent, an antidiabetic agent, an antipsychotic agent, a prostatomegaly agent, an anti-asthma agent, a drug with a short pharmacokinetic half-life, pharmaceutically acceptable salts thereof, derivatives thereof, and combinations thereof.

28. The composition of claim 27, wherein said proton pump inhibitor is selected from the group consisting of omeprazole, esomeprazole, lansoprazole, rabeprazole, pantoprazole, pharmaceutically acceptable salts thereof, derivatives thereof, and combinations thereof.

29. The composition of claim 23, wherein said drug core further comprises a buffering agent.

30. The composition of claim 23, wherein said enteric coat further comprises a buffering agent.

31. The composition of claim 23, wherein said saccharide is selected from the group consisting of lactulose, raffinose, cellobiose, stachyose, fructoligosaccharide, sucrose, glucose, xylose, fructose, mannitol, maltose, galactose, and combinations thereof.

32. The composition of claim 31, wherein said saccharide is lactulose.

33. The composition of claim 31, wherein said saccharide is present in an amount of from about 10% to about 90% w/w.

34. The composition of claim 23, wherein said organic acid-soluble polymer is selected from the group consisting of a dimethylaminoethyl methacrylate-methyl methacrylate copolymer, a polyvinyl acetal diethylaminoacetate, chitosan, and combinations thereof.

35. The composition of claim 34, wherein said dimethylaminoethyl methacrylate-methyl methacrylate copolymer is a dimethylaminoethyl methacrylate-methyl methacrylate-butyl methacrylate copolymer.

36. The composition of claim 34, wherein said organic acid-soluble polymer is present in an amount of from about 2.5% to about 40.0% w/w.

37. The composition of claim 34, wherein said organic acid-soluble polymer dissolves at a pH lower than about 6.

38. The composition of claim 23, wherein said water-permeable, release-controlling polymer is selected from the group consisting of a copolymer of ethyl acrylate, methyl methyacrylate, and trimethylammonio ethyl methacrylate chloride, ethyl cellulose, hydroxypropylmethylcellulose (HPMC), hydroxypropylcellulose, polyethylene oxide, polyvinylpyrrolidone, and combinations thereof.

39. The composition of claim 38, wherein said water-permeable, release-controlling polymer is HPMC.

40. The composition of claim 23, wherein said enteric coating polymer is selected from the group consisting of a methyl methacrylate-methylacrylate acid (1:1) copolymer, a methyl methacrylate-methacrylate acid (2:1) copolymer, an ethyl acrylate-methacrylic acid (1:1) copolymer, hydroxypropylmethylcellulose phthalate, cellulose acetate phthalate, shellac, and combinations thereof.

41. The composition of claim 23, further comprising an outer drug coat having a third drug, wherein said enteric coat is coated by said outer drug coat and said composition releases said third drug in the stomach.

42. The composition of claim 23, wherein said composition is in the form of a tablet or granule.

* * * * *